United States Patent
Callahan

(10) Patent No.: US 9,408,546 B2
(45) Date of Patent: Aug. 9, 2016

(54) RADIOLUCENT ECG ELECTRODE SYSTEM

(71) Applicant: Covidien LP, Mansfield, MA (US)

(72) Inventor: Mark Callahan, Medway, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/987,326

(22) Filed: Mar. 15, 2013

(65) Prior Publication Data
US 2014/0303472 A1 Oct. 9, 2014

(51) Int. Cl.
H01R 4/48 (2006.01)
A61B 5/0416 (2006.01)

(52) U.S. Cl.
CPC ......... *A61B 5/0416* (2013.01); *A61B 2562/225* (2013.01)

(58) Field of Classification Search
USPC .......... 439/729, 18, 864, 773, 909, 157, 553, 439/838, 261, 859, 733; 600/386, 394, 733, 600/509
See application file for complete search history.

(56) References Cited

U.S. PATENT DOCUMENTS

| | | | |
|---|---|---|---|
| 3,606,881 A | 9/1971 | Woodson | |
| 3,752,151 A | 8/1973 | Robichaud | |
| 3,805,769 A | 4/1974 | Sessions | |
| 3,828,766 A | 8/1974 | Krasnow | |
| 3,829,826 A | 8/1974 | Brown et al. | |
| 3,842,394 A | 10/1974 | Bolduc | |
| 3,868,946 A | 3/1975 | Hurley | |
| 3,888,240 A | 6/1975 | Reinhold, Jr. et al. | |
| 3,895,635 A | 7/1975 | Justus et al. | |
| 3,901,218 A | 8/1975 | Buchalter | |
| 3,997,225 A | 12/1976 | Horwinski | |
| 3,998,213 A | 12/1976 | Price | |
| 4,027,664 A | 6/1977 | Heavner, Jr. et al. | |
| 4,034,854 A | 7/1977 | Bevilacqua | |
| 4,077,397 A | 3/1978 | Ellis et al. | |

(Continued)

FOREIGN PATENT DOCUMENTS

| | | |
|---|---|---|
| CN | 101491437 A | 7/2009 |
| CN | 101491438 | 7/2009 |

(Continued)

OTHER PUBLICATIONS

International Search Report and Written Opinion dated Sep. 9, 2014 for PCT Application No. PCT/US2014/027328; 16 pages.

(Continued)

*Primary Examiner* — Alexander Gilman

(57) ABSTRACT

Disclosed is an ECG electrode lead system suitable for use during imaging procedures such as, without limitation, CT scans or MRI and methods of use. In embodiments, the system includes an ECG electrode connector formed from radiolucent materials to enhance performance during imaging procedures by reducing or eliminating shadows on imaging media. In some embodiments, the disclosed connector includes a housing having an opening configured to operably receive an electrode post of an ECG electrode pad, an electrode member having a generally semicircular contact face disposed along at least a part of the perimeter of the opening, and an engagement member having an actuation surface and an engaging face pivotable about a pivot to enable engaging face to move from a first position whereby the engaging face is closer to the contact face and a second position whereby the engaging face is further from the contact face.

20 Claims, 11 Drawing Sheets

(56) References Cited

U.S. PATENT DOCUMENTS

| | | | |
|---|---|---|---|
| 4,112,941 A | 9/1978 | Larimore | |
| 4,166,465 A | 9/1979 | Esty et al. | |
| 4,220,390 A | 9/1980 | Cobaugh et al. | |
| 4,303,293 A | 12/1981 | Grunwald | |
| D263,167 S | 2/1982 | Stone | |
| 4,353,372 A | 10/1982 | Ayer | |
| 4,365,634 A | 12/1982 | Bare et al. | |
| 4,498,480 A | 2/1985 | Mortensen | |
| 4,674,817 A | 6/1987 | Olms | |
| 4,729,377 A | 3/1988 | Granek et al. | |
| 4,763,660 A | 8/1988 | Kroll et al. | |
| 4,781,200 A | 11/1988 | Baker | |
| 4,785,822 A | 11/1988 | Wallace | |
| 4,815,964 A | 3/1989 | Cohen et al. | |
| 4,842,557 A | 6/1989 | Muz | |
| 4,850,356 A | 7/1989 | Heath | |
| 4,909,260 A | 3/1990 | Salem et al. | |
| 4,947,846 A | 8/1990 | Kitagawa et al. | |
| 4,957,109 A | 9/1990 | Groeger et al. | |
| 4,974,594 A | 12/1990 | Berlin | |
| 5,080,604 A | 1/1992 | Rider et al. | |
| 5,083,238 A | 1/1992 | Bousman | |
| 5,083,933 A | 1/1992 | Colleran et al. | |
| 5,104,253 A | 4/1992 | Zielinski et al. | |
| 5,104,334 A | 4/1992 | Honma et al. | |
| 5,131,854 A | 7/1992 | Jose et al. | |
| 5,137,466 A | 8/1992 | Endo et al. | |
| 5,154,646 A | 10/1992 | Shoup | |
| 5,158,469 A | 10/1992 | Martin | |
| 5,160,276 A | 11/1992 | Marsh et al. | |
| 5,173,059 A | 12/1992 | Sato et al. | |
| 5,176,343 A | 1/1993 | Cheney et al. | |
| 5,178,556 A | 1/1993 | Chen | |
| 5,180,312 A | 1/1993 | Martin | |
| 5,190,467 A | 3/1993 | Ohta | |
| 5,192,226 A | 3/1993 | Wang | |
| 5,197,901 A | 3/1993 | Hashiguchi | |
| 5,199,897 A | 4/1993 | Hashiguchi | |
| 5,201,669 A | 4/1993 | Lin | |
| 5,203,715 A | 4/1993 | Yamamoto | |
| 5,203,719 A | 4/1993 | Kozono | |
| 5,207,594 A | 5/1993 | Olson | |
| 5,224,479 A | 7/1993 | Sekine | |
| 5,232,383 A | 8/1993 | Barnick | |
| 5,234,357 A | 8/1993 | Yamaguchi | |
| 5,243,510 A | 9/1993 | Cheney | |
| 5,263,481 A | 11/1993 | Axelgaard | |
| 5,276,443 A | 1/1994 | Gates et al. | |
| 5,278,759 A | 1/1994 | Berra et al. | |
| 5,279,308 A | 1/1994 | DiSabito et al. | |
| 5,293,013 A | 3/1994 | Takahashi | |
| 5,320,621 A | 6/1994 | Gordon et al. | |
| 5,326,272 A | 7/1994 | Harhen et al. | |
| 5,332,330 A | 7/1994 | Kaneko | |
| 5,338,219 A | 8/1994 | Hiramoto | |
| 5,341,806 A | 8/1994 | Gadsby et al. | |
| 5,341,812 A | 8/1994 | Allaire et al. | |
| 5,353,793 A | 10/1994 | Bornn | |
| 5,354,216 A * | 10/1994 | Cruise et al. | 439/553 |
| 5,362,249 A | 11/1994 | Carter | |
| 5,370,116 A | 12/1994 | Rollman et al. | |
| 5,370,550 A | 12/1994 | Alwine et al. | |
| 5,376,016 A | 12/1994 | Inaba et al. | |
| 5,378,168 A | 1/1995 | Sumida | |
| 5,380,223 A | 1/1995 | Marsh et al. | |
| 5,382,176 A | 1/1995 | Norden | |
| 5,383,794 A | 1/1995 | Davis et al. | |
| 5,387,116 A | 2/1995 | Wang | |
| 5,387,127 A | 2/1995 | Wang | |
| 5,399,045 A | 3/1995 | Yoneda et al. | |
| 5,405,269 A | 4/1995 | Stupecky | |
| 5,415,164 A | 5/1995 | Faupel et al. | |
| 5,429,526 A | 7/1995 | Ann | |
| 5,431,166 A | 7/1995 | Macur | |
| 5,454,739 A | 10/1995 | Strand | |
| 5,462,448 A | 10/1995 | Kida et al. | |
| 5,484,739 A | 1/1996 | Lee et al. | |
| 5,486,117 A | 1/1996 | Chang | |
| 5,507,290 A | 4/1996 | Kelly et al. | |
| 5,507,665 A | 4/1996 | Oda | |
| 5,507,668 A | 4/1996 | Lambrinos et al. | |
| 5,509,822 A | 4/1996 | Negus et al. | |
| 5,511,553 A | 4/1996 | Segalowitz | |
| 5,546,950 A | 8/1996 | Schoeckert et al. | |
| 5,558,535 A | 9/1996 | Saka et al. | |
| 5,564,939 A | 10/1996 | Maitani et al. | |
| 5,582,180 A | 12/1996 | Manset et al. | |
| 5,584,719 A | 12/1996 | Tsuji et al. | |
| D377,219 S | 1/1997 | Strand et al. | |
| 5,599,199 A | 2/1997 | Wright | |
| 5,603,632 A | 2/1997 | Johannes et al. | |
| 5,611,708 A | 3/1997 | Mizunuma et al. | |
| 5,613,870 A | 3/1997 | Traver, Jr. | |
| 5,615,674 A | 4/1997 | Maurer | |
| 5,622,168 A | 4/1997 | Keusch et al. | |
| 5,624,271 A | 4/1997 | Childs et al. | |
| 5,624,281 A | 4/1997 | Christensson | |
| 5,626,135 A | 5/1997 | Sanfilippo | |
| 5,632,274 A | 5/1997 | Quedens et al. | |
| 5,651,689 A | 7/1997 | Plyler et al. | |
| 5,653,606 A | 8/1997 | Chrysostomou | |
| 5,674,088 A | 10/1997 | Roche et al. | |
| 5,676,694 A | 10/1997 | Boser et al. | |
| 5,679,022 A | 10/1997 | Cappa | |
| 5,679,029 A | 10/1997 | Saunier et al. | |
| 5,685,303 A | 11/1997 | Rollman et al. | |
| 5,695,355 A | 12/1997 | Hasenfratz et al. | |
| 5,702,265 A | 12/1997 | Yamaguchi | |
| 5,704,351 A | 1/1998 | Mortara et al. | |
| 5,711,684 A | 1/1998 | Inoue et al. | |
| 5,718,596 A | 2/1998 | Inaba et al. | |
| 5,724,025 A | 3/1998 | Tavori | |
| 5,724,984 A | 3/1998 | Arnold et al. | |
| 5,725,525 A | 3/1998 | Kordis | |
| 5,741,155 A | 4/1998 | Herman | |
| 5,749,746 A | 5/1998 | Tan et al. | |
| 5,769,650 A | 6/1998 | Aoyama et al. | |
| 5,772,591 A | 6/1998 | Cram | |
| 5,775,953 A | 7/1998 | Yamanashi et al. | |
| 5,782,647 A | 7/1998 | Okura et al. | |
| 5,782,761 A | 7/1998 | Gusakov | |
| 5,782,892 A | 7/1998 | Castle et al. | |
| 5,788,527 A | 8/1998 | Sanders et al. | |
| 5,791,918 A | 8/1998 | Pierce | |
| 5,797,854 A | 8/1998 | Hedgecock | |
| 5,806,152 A | 9/1998 | Saitou et al. | |
| 5,813,404 A | 9/1998 | Devlin et al. | |
| 5,813,979 A | 9/1998 | Wolfer | |
| 5,827,086 A | 10/1998 | Fukuda | |
| 5,830,000 A | 11/1998 | Shifflett et al. | |
| 5,836,783 A | 11/1998 | Morisawa et al. | |
| 5,843,141 A | 12/1998 | Bischoff et al. | |
| 5,848,456 A | 12/1998 | Sjoqvist | |
| 5,865,740 A | 2/1999 | Kelly et al. | |
| 5,865,741 A | 2/1999 | Kelly et al. | |
| 5,871,451 A | 2/1999 | Unger et al. | |
| 5,873,747 A | 2/1999 | Tsuji | |
| 5,876,232 A | 3/1999 | Matsushita et al. | |
| 5,895,284 A | 4/1999 | Kocher et al. | |
| 5,895,298 A | 4/1999 | Faupel | |
| 5,904,579 A | 5/1999 | McLean et al. | |
| 5,913,834 A | 6/1999 | Francais | |
| 5,916,159 A | 6/1999 | Kelly et al. | |
| 5,931,689 A | 8/1999 | Patel | |
| 5,931,861 A | 8/1999 | Werner et al. | |
| 5,934,926 A | 8/1999 | Gabrisko, Jr. et al. | |
| 5,937,950 A | 8/1999 | Adams et al. | |
| 5,938,470 A | 8/1999 | Kashiyama | |
| 5,938,597 A | 8/1999 | Starbucker | |
| 5,941,725 A | 8/1999 | Brennan et al. | |
| 5,944,562 A * | 8/1999 | Christensson | A61B 5/0416 439/261 |
| 5,951,316 A | 9/1999 | Kawano et al. | |
| 5,964,624 A | 10/1999 | Pernelle | |

(56) References Cited

U.S. PATENT DOCUMENTS

| | | | |
|---|---|---|---|
| 5,968,087 A | 10/1999 | Hess et al. |
| 5,971,790 A | 10/1999 | Rohde |
| 5,971,799 A | 10/1999 | Swade |
| 5,980,332 A | 11/1999 | Tsuji et al. |
| 5,984,717 A | 11/1999 | Lee |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,038,479 A | 3/2000 | Werner et al. |
| 6,038,481 A | 3/2000 | Werner et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,190,385 B1 | 2/2001 | Tom et al. |
| 6,203,354 B1 | 3/2001 | Kuwahara |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,312,297 B1 * | 11/2001 | Lorkowski ............... 439/838 |
| 6,324,432 B1 | 11/2001 | Rigaux et al. |
| D452,318 S | 12/2001 | Merry et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,363,272 B1 | 3/2002 | Combs |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisandier |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wi |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| 6,816,744 B2 | 11/2004 | Garfield et al. |
| 6,832,928 B2 | 12/2004 | Suzuki et al. |
| 6,837,734 B2 | 1/2005 | Ushio et al. |
| 6,847,836 B1 | 1/2005 | Sujdak |
| 6,848,926 B2 | 2/2005 | Ling et al. |
| 6,851,969 B2 | 2/2005 | Archuletta |
| 6,860,750 B1 | 3/2005 | Wu |
| 6,866,535 B2 | 3/2005 | Uchida |
| 6,881,098 B2 | 4/2005 | Jeansonne et al. |

(56) References Cited

U.S. PATENT DOCUMENTS

| | | | |
|---|---|---|---|
| 6,891,379 B2 | 5/2005 | Kelly et al. | |
| 6,913,482 B1 | 7/2005 | Wu | |
| 6,939,158 B2 | 9/2005 | Moffett et al. | |
| 6,939,345 B2 | 9/2005 | Knight et al. | |
| 6,945,796 B2 | 9/2005 | Bassler et al. | |
| 6,945,807 B1 | 9/2005 | Wu | |
| 6,948,973 B1 | 9/2005 | Hsu et al. | |
| 6,970,731 B1 | 11/2005 | Jayaraman et al. | |
| 6,973,341 B2 | 12/2005 | Watson | |
| 6,973,343 B2 | 12/2005 | Wenger | |
| 6,980,852 B2 | 12/2005 | Jersey-Willuhn et al. | |
| 6,984,143 B2 | 1/2006 | Roese | |
| 6,997,733 B2 | 2/2006 | Peng | |
| 7,004,787 B2 | 2/2006 | Milan | |
| 7,008,255 B1 | 3/2006 | Wang | |
| 7,025,618 B2 | 4/2006 | Fukuda | |
| 7,025,628 B2 | 4/2006 | LaMeres et al. | |
| 7,029,286 B2 | 4/2006 | Hall et al. | |
| 7,033,207 B2 | 4/2006 | Nimura | |
| 7,041,918 B1 | 5/2006 | Wu | |
| 7,056,134 B2 | 6/2006 | Martin et al. | |
| 7,056,141 B2 | 6/2006 | Moffett et al. | |
| 7,077,711 B1* | 7/2006 | Moore | 439/864 |
| 7,081,008 B2 | 7/2006 | Tan | |
| 7,081,026 B2 | 7/2006 | Schwarz | |
| 7,083,480 B2 | 8/2006 | Silber | |
| 7,085,598 B2 | 8/2006 | Sato | |
| 7,104,801 B1 | 9/2006 | Brodnick et al. | |
| 7,110,804 B2 | 9/2006 | Baumer et al. | |
| 7,117,590 B2 | 10/2006 | Koenig et al. | |
| 7,118,411 B2 | 10/2006 | Huang et al. | |
| 7,127,279 B2 | 10/2006 | Finneran et al. | |
| 7,128,600 B2 | 10/2006 | Osypka | |
| 7,134,908 B2 | 11/2006 | Wu | |
| 7,137,839 B2 | 11/2006 | Dilliner et al. | |
| 7,144,268 B2 | 12/2006 | Koenig et al. | |
| 7,150,655 B2 | 12/2006 | Mastrototaro et al. | |
| D535,029 S | 1/2007 | McAtamney et al. | |
| 7,160,136 B2 | 1/2007 | Zhang et al. | |
| 7,169,107 B2 | 1/2007 | Jersey-Willuhn et al. | |
| 7,179,111 B2 | 2/2007 | Van Der Mee et al. | |
| 7,179,113 B2 | 2/2007 | Koenig et al. | |
| 7,182,630 B1 | 2/2007 | Su | |
| 7,184,820 B2 | 2/2007 | Jersey-Willuhn et al. | |
| 7,189,097 B2 | 3/2007 | Benham | |
| 7,197,357 B2 | 3/2007 | Istvan et al. | |
| 7,198,502 B2 | 4/2007 | Koenig et al. | |
| 7,201,599 B2 | 4/2007 | Holub | |
| 7,207,825 B2 | 4/2007 | Le Gallic et al. | |
| 7,214,107 B2 | 5/2007 | Powell et al. | |
| 7,236,825 B2 | 6/2007 | Wang | |
| 7,252,542 B2 | 8/2007 | Chen | |
| 7,252,556 B2 | 8/2007 | Anbo et al. | |
| 7,252,565 B2 | 8/2007 | Hunter | |
| 7,255,609 B1 | 8/2007 | Epstein | |
| 7,258,566 B2 | 8/2007 | Koenig et al. | |
| 7,264,510 B2 | 9/2007 | Koenig et al. | |
| 7,270,568 B2 | 9/2007 | Osypka | |
| 7,270,580 B2 | 9/2007 | Bradley et al. | |
| 7,272,427 B2 | 9/2007 | Ristolainen | |
| 7,272,428 B2 | 9/2007 | Hopman et al. | |
| 7,275,951 B2 | 10/2007 | Shigeta et al. | |
| 7,281,937 B2 | 10/2007 | Reed et al. | |
| 7,287,998 B2 | 10/2007 | Masai | |
| 7,303,430 B2 | 12/2007 | Butcher | |
| 7,318,740 B1 | 1/2008 | Henry et al. | |
| 7,319,895 B2 | 1/2008 | Klefstad-Sillinville et al. | |
| 7,322,849 B2 | 1/2008 | Sutton | |
| 7,329,139 B2 | 2/2008 | Benham | |
| 7,333,850 B2 | 2/2008 | Marossero et al. | |
| 7,347,710 B2 | 3/2008 | Ohtaka et al. | |
| 7,347,826 B1 | 3/2008 | Karicherla et al. | |
| 7,359,751 B1 | 4/2008 | Erickson et al. | |
| 7,361,058 B1 | 4/2008 | Lien et al. | |
| 7,364,440 B2 | 4/2008 | Gobron et al. | |
| 7,371,102 B2 | 5/2008 | Sakamoto et al. | |
| 7,373,196 B2 | 5/2008 | Ryu et al. | |
| 7,374,448 B1 | 5/2008 | Jepsen et al. | |
| 7,381,082 B2 | 6/2008 | Lai | |
| 7,390,224 B2 | 6/2008 | Sodemann et al. | |
| 7,396,246 B2 | 7/2008 | Okada et al. | |
| 7,399,195 B2 | 7/2008 | Kim et al. | |
| 7,401,946 B2 | 7/2008 | Laukhuf | |
| 7,402,071 B2 | 7/2008 | Ohtaka et al. | |
| 7,413,461 B2 | 8/2008 | Dawiedczyk et al. | |
| 7,413,485 B2 | 8/2008 | Lappoehn | |
| 7,416,440 B2 | 8/2008 | Homyk et al. | |
| 7,422,437 B1 | 9/2008 | Lin et al. | |
| 7,422,452 B2 | 9/2008 | Achter et al. | |
| 7,445,512 B1 | 11/2008 | Lai | |
| 7,445,522 B2 | 11/2008 | Burns | |
| 7,462,074 B1 | 12/2008 | Devlin et al. | |
| 7,473,141 B2 | 1/2009 | Liao | |
| 7,488,187 B2 | 2/2009 | Wolf | |
| 7,494,383 B2 | 2/2009 | Cohen et al. | |
| 7,497,738 B2 | 3/2009 | Kuo | |
| 7,503,807 B2 | 3/2009 | Martin et al. | |
| 7,556,535 B2 | 7/2009 | Liao | |
| 7,581,992 B1 | 9/2009 | Liu et al. | |
| 7,585,182 B2 | 9/2009 | Asante et al. | |
| 7,591,673 B2 | 9/2009 | Chan et al. | |
| 7,604,511 B1 | 10/2009 | Johnson | |
| 7,618,377 B2 | 11/2009 | McAtamney et al. | |
| 7,632,130 B2 | 12/2009 | Sami | |
| 7,666,028 B2 | 2/2010 | Meleck | |
| D629,358 S | 12/2010 | Slippy et al. | |
| 7,950,971 B2 | 5/2011 | Hobet et al. | |
| 8,038,484 B2* | 10/2011 | Selvitelli et al. | 439/729 |
| 8,152,571 B2* | 4/2012 | Selvitelli et al. | 439/729 |
| 8,255,041 B2 | 8/2012 | Istvan et al. | |
| D675,738 S | 2/2013 | Baumer et al. | |
| 8,408,507 B2* | 4/2013 | Liu | 248/230.4 |
| 8,408,948 B2 | 4/2013 | Selvitelli et al. | |
| 8,414,315 B2* | 4/2013 | Dekoski | 439/157 |
| D689,614 S | 9/2013 | Browne et al. | |
| D699,360 S | 2/2014 | Maryzynski et al. | |
| 8,690,611 B2* | 4/2014 | Selvitelli et al. | 439/729 |
| 8,694,080 B2 | 4/2014 | Farrior | |
| 8,795,004 B2* | 8/2014 | Selvitelli et al. | 439/729 |
| D718,867 S | 12/2014 | Schroderus | |
| 2001/0053639 A1* | 12/2001 | Endo | 439/773 |
| 2002/0133069 A1 | 9/2002 | Roberts | |
| 2002/0138011 A1 | 9/2002 | Rantala | |
| 2002/0188216 A1 | 12/2002 | Kayyali et al. | |
| 2003/0068914 A1 | 4/2003 | Merry et al. | |
| 2003/0068918 A1 | 4/2003 | Christensson | |
| 2004/0073127 A1 | 4/2004 | Istvan et al. | |
| 2004/0127802 A1 | 7/2004 | Istvan et al. | |
| 2004/0176674 A1 | 9/2004 | Nazeri | |
| 2004/0203273 A1 | 10/2004 | Schwarz | |
| 2005/0164551 A1 | 7/2005 | Wlos | |
| 2005/0177052 A1 | 8/2005 | Istvan et al. | |
| 2005/0203349 A1 | 9/2005 | Nanikashvili | |
| 2006/0073728 A1 | 4/2006 | Zaiken et al. | |
| 2006/0110962 A1 | 5/2006 | Powell et al. | |
| 2006/0286861 A1 | 12/2006 | Avevor et al. | |
| 2007/0038057 A1 | 2/2007 | Nam et al. | |
| 2007/0260133 A1 | 11/2007 | Meyer | |
| 2008/0132106 A1 | 6/2008 | Burnes et al. | |
| 2008/0132773 A1 | 6/2008 | Burnes et al. | |
| 2008/0177168 A1 | 7/2008 | Callahan et al. | |
| 2009/0099423 A1 | 4/2009 | Al-Ali et al. | |
| 2009/0149731 A1* | 6/2009 | Selvitelli | A61B 5/0416 600/394 |
| 2009/0221153 A1* | 9/2009 | Santangelo et al. | 439/18 |
| 2011/0092833 A1 | 4/2011 | Farrior | |
| 2011/0275252 A1* | 11/2011 | Selvitelli et al. | 439/729 |
| 2012/0196474 A1 | 8/2012 | Selvitelli et al. | |
| 2013/0023750 A1* | 1/2013 | Callahan | A61B 5/04286 600/386 |
| 2013/0189881 A1* | 7/2013 | Selvitelli et al. | 439/729 |

(56) References Cited

U.S. PATENT DOCUMENTS

| | | | |
|---|---|---|---|
| 2014/0170896 A1* | 6/2014 | Selvitelli et al. | 439/449 |
| 2014/0180148 A1 | 6/2014 | Coggins et al. | |
| 2014/0309514 A1* | 10/2014 | Zhou | A61B 5/0416 600/394 |

FOREIGN PATENT DOCUMENTS

| | | |
|---|---|---|
| DE | 9002539 U1 | 5/1990 |
| DE | 10225621 | 1/2004 |
| DE | 102004032410 | 1/2006 |
| EP | 0 766 946 A2 | 4/1997 |
| EP | 0 799 628 | 10/1997 |
| EP | 1 050 269 | 11/2000 |
| EP | 1645224 | 4/2008 |
| EP | 1 932 470 | 6/2008 |
| EP | 2 070 474 | 6/2009 |
| GB | 162804 | 5/1921 |
| JP | 10248820 A | 9/1998 |
| JP | 2003/010138 | 1/2003 |
| JP | 2004/282608 | 10/2004 |
| WO | WO 03 47427 | 6/2003 |
| WO | WO 2008/092098 A2 | 7/2008 |
| WO | WO 2013/013370 A1 | 1/2013 |

OTHER PUBLICATIONS

Office Action dated Sep. 10, 2014 for U.S. Appl. No. 14/324,380; 7 pages.
A&D Company, Limited, "Vital Sensor Graphic Model", No. TM-2560G/TM2564G-TM-2564GP/TM2564GP, Jan. 1, 2004; pp. 1-62.
Andreas Boos et al.; "A New Lightweight Fetal Telemetry System", Dec. 1995; Hewlett-Packard Journal; 12 pages.
Tyco Healthcare Kendal, ECG Electrodes Where Quality leads 2003 8 pages.
European Search Report Corresponding to European Application No. EP 07 25 3850, Date of completion is Dec. 21, 2007 3 pages.
EP Notice Under Rule161 dated Feb. 28, 2014, for EP App. No. 11869957.8 3 pages.
Response to Written Opinion and Claims Filed on Jun. 11, 2014, for EP App. No. 11869957.8 6 pages.
Search Report and Written Opinion dated Apr. 12, 2012, for App. No. PCT/CN2011/077506 14 pages.
First Office Action dated Jul. 26, 2011, for Chinese App. No. 200810191090.1 6 pages.
Letter regarding Response to Office Action dated Nov. 22, 2011, for Chinese App. No. 200810191090.1 9 pages.
Response to Office Action dated Dec. 12, 2011, for Chinese App. No. 200810191090.1 18 pages.
Letter dated May 11, 2012 enclosing Second Office Action dated Apr. 27, 2012, for Chinese App. No. 200810191090.1 6 pages.
Notification of Response to Second Office Action dated Jun. 11, 2012, for Chinese App. No. 200810191090.1 5 pages.
Letter dated Dec. 20, 2012 enclosing Grant Notification dated Dec. 19, 2012, for Chinese App. No. 200810191090.1 4 pages.
Divisional Application as filed on Mar. 1, 2013, for Chinese App. No. 200810191090.1 37 pages.
European Office Action dated Nov. 19, 2010, for EP App. No. 08171185.5 1 page.
Letter dated Dec. 22, 2010 in response to EP Office Action Nov. 19, 2010 European Office Action for EP App. No. 08171185.5 1 page.
Response to Office Action dated Oct. 3, 2012 for EP App. No. 08171185.5 2 page.
Letter dated Oct. 4, 2012 and copy of Divisional for EP App. No. 08171185.5 39 pages.
Letter dated Dec. 16, 2013 In response to Communication dated Jun. 24, 2013, for EP App. No. 08171185.5 4 pages.
Examination Report dated Jun. 24, 2013, for EP App. No. 08171185.5 4 pages.
Extended Search Report dated Mar. 7, 2012, for EP App. No. 08171185.5 8 pages.
Letter dated Apr. 2, 2012 and Office Action for Mexican App. No. MX/a/2008/015927 3 pages.
Letter dated May 15, 2012 and Response to Office Action for Mexican App. No. MX/a/2008/015927 Filed on Dec. 11, 2008 9 Pages.
Letter dated Jun. 26, 2012 and Regarding Notice of Allowance with allowed claims for Mexican App. No. MX/a/2008/015927 Filed on Dec. 11, 2008 7 Pages.
Letter dated Feb. 5, 2014 Confirming receipt of Notice of Allowance. for Mexican App. No. MX/a/2012/009542 2 pages.
Letter dated Feb. 25, 2013 also enclosing Office Action for App. No. MX/a/2012/009542 3 pages.
Letter and Response to Office Action dated Apr. 23, 2013, for Mexican App. No. MX/a/2012/009542 20 pages.
Letter dated Sep. 18, 2013 And Office Action for Mexican App. No. MX/a/2012/009542 4 pages.
Letter dated Oct. 30, 2013 And Response to Office Action for Mexican App. No. MX/a/2012/009542 5 pages.
Letter dated Jun. 10, 2014 Confirming receipt of Notice Of Allowance for Mexican App. No. MX/a/2013/012636 2 pages.
Letter dated Jun. 10, 2014 Confirming receipt of Notice Of Allowance for Mexican App. No. MX/a/2013/012635 2 pages.
Extended Search Report dated Oct. 8, 2013, for EP App. No. 12187209.7009542 6 pages.
European Notice Responding to Search Report dated Nov. 11, 2013, For EP App. No. 12187209.7009542 2 pages.
European Exam Report dated Mar. 11, 2014, for EP App. No. 12187209.7009542 4 pages.
Response dated Jan. 27, 2014 to Extended Search Report dated Oct. 8, 2013, for EP App. No. 12187209.7009542 16 pages.
Response to Exam Report dated Jun. 24, 2014 for EP App. No. 12187209.7009542 8 pages.
Response dated Nov. 2, 2011 to Communication dated May 10, 2011 for EP App. No. 10013624.10 5 pages.
Extended Search Report dated Apr. 4, 2011, for EP App. No. 10013624.10 14 pages.
European Exam Report dated Nov. 12, 2013, for EP App. No. 12187209.7009542 6 pages.
Response to Communication dated Mar. 17, 2014 for EP App. No. 12187209.7009542 14 pages.
European Office Action dated May 21, 2014 for EP App. No. 12187209.7009542 5 pages.
European Search Report dated May 23, 2014, for EP App. No. 14162076.5 10 pages.
Response to Chinese Office Action dated May 4, 2011, for Chinese App. No. 201010624971.50 21 pages.
Notification of Entry into Examination Procedure dated Oct. 11, 2012, for Chinese App. No. 201010624971.50 2 Pages.
Receipt of First Office Action dated Nov. 28, 2013, for Chinese App. No. 201010624971.50 136 Pages.
Response to Office Action dated Apr. 14, 2014, for Chinese App. No. 201010624971.50 34 Pages.
Search Report dated Jun. 4, 2014, for App. No. PCT/US2014/019479 10 pages.
Article 19 Amendment as filed dated Jul. 2, 2014 for App. No. PCT/US2014/019479 10 pages.
Letter and Chinese Office Action dated Jul. 1, 2014, for Chinese App. No. 2013100649128.3 38 pages.
Voluntary Amendment with English claims dated Jul. 15, 2014 for Application No. 201180072455.9 7 pages.
Preliminary Amendment dated Jul. 7, 2014 for Application No. 14/324,380 6 pages.
Partial Search Report dated Jun. 5, 2014 for Application No. PCT/US2014/027328 6 pages.
Simpson U.S. Appl. No. 14/209,278, filed Mar. 13, 2014 30 pages.
Zhou U.S. Appl. No. 14/160,798, filed Jan. 22, 2014 26 pages.
Selvitelli U.S. Appl. No. 14/324,380, filed Jul. 7, 2014 41 pages.
U.S. Appl. No. 12/330,550; 175 Pages.
U.S. Appl. No. 13/182,656; 143 pages.
U.S. Appl. No. 13/443,096; 50 pages.
U.S. Appl. No. 13/785,713, filed Mar. 5, 2013, 200pages, Part 1.
U.S. Appl. No. 13/785,713, filed Mar. 5, 2013, 200 pages, Part 2.

(56) References Cited

OTHER PUBLICATIONS

U.S. Appl. No. 13/785,713, filed Mar. 5, 2013, 200 pages, Part 3.
U.S. Appl. No. 13/785,713, filed Mar. 5, 2013, 200 pages, Part 4.
U.S. Appl. No. 13/785,713, filed Mar. 5, 2013, 200 pages, Part 5.
U.S. Appl. No. 13/785,713, filed Mar. 5, 2013, 200 pages, Part 6.
U.S. Appl. No. 13/785,713, filed Mar. 5, 2013, 200 pages, Part 7.
U.S. Appl. No. 13/785,713, filed Mar. 5, 2013, 200 pages, Part 8.
U.S. Appl. No. 13/785,713, filed Mar. 5, 2013, 200 pages, Part 9.
U.S. Appl. No. 13/785,713, filed Mar. 5, 2013, 200 pages, Part 10.
U.S. Appl. No. 13/785,713, filed Mar. 5, 2013, 200 pages, Part 11.
U.S. Appl. No. 13/785,713, filed Mar. 5, 2013, 200 pages, Part 12.
U.S. Appl. No. 13/785,713, filed Mar. 5, 2013, 200 pages, Part 13.
U.S. Appl. No. 13/785,713, filed Mar. 5, 2013, 18 pages, Part 14.
U.S. Appl. No. 14/041,471; Part 1 of 16; 350 Pages.
U.S. Appl. No. 14/041,471; Part 2 of 16; 350 Pages.
U.S. Appl. No. 14/041,471; Part 3 of 16; 350 Pages.
U.S. Appl. No. 14/041,471; Part 4 of 16; 350 Pages.
U.S. Appl. No. 14/041,471; Part 5 of 16; 350 Pages.
U.S. Appl. No. 14/041,471; Part 6 of 16; 350 Pages.
U.S. Appl. No. 14/041,471; Part 7 of 16; 350 Pages.
U.S. Appl. No. 14/041,471; Part 8 of 16; 350 Pages.
U.S. Appl. No. 14/041,471; Part 9 of 16; 150 Pages.
U.S. Appl. No. 14/041,471; Part 9A of 16; 200 Pages.
U.S. Appl. No. 14/041,471; Part 10 of 16; 350 Pages.
U.S. Appl. No. 14/041,471; Part 11 of 16; 350 Pages.
U.S. Appl. No. 14/041,471; Part 12 of 16; 350 Pages.
U.S. Appl. No. 14/041,471; Part 13 of 16; 350 Pages.
U.S. Appl. No. 14/041,471. Part 14 of 16; 350 Pages.
U.S. Appl. No. 14/041,471; Part 15 of 16; 350 Pages.
U.S. Appl. No. 14/041,471 Part 16 of 16; 138 Pages.
U.S. Appl. No. 12/876,316; Part 1 of 5; 250 Pages.
U.S. Appl. No. 12/876,316; Part 2 of 5; 250 Pages.
U.S. Appl. No. 12/876,316; Part 3 of 5; 250 Pages.
U.S. Appl. No. 12/876,316; Part 4 of 5; 250 Pages.
U.S. Appl. No. 12/876,316; Part 5 of 5; 238 Pages.
U.S. Appl. No. 14/195,140; 314 Pages.
Response filed Feb. 6, 2015; for Office Action dated Sep. 10, 2014; for U.S. Appl. No. 14/324,380; 8 pages.
Chinese Office Action dated Jan. 12, 2015; with English Translation for Chinese App. No. 200180072455.9; 15 pages.
Response to Chinese Office Action filed Oct. 24, 2014 with English translation for Chinese Application No. 201310064924.3; 27 pages.
Letter from CCPIT Patent and Trademark Law Office dated Jan. 2, 2015 for Chinese Application No. 201310064924.3; 7 pages.
Chinese Office Action dated Nov. 17, 2014 for Chinese Application No. 201310064924.3, 3 pages.
European Extended Search Report dated Nov. 18, 2014 for European Application No. 11869957.8; 9 pages.
European Search Report dated Apr. 17, 2015 for European Application No. 14197698.5; 7 pages.
Notice of Allowance dated Mar. 31, 2015 for U.S. Appl. No. 14/324,380; 9 pages.
Office Action dated Apr. 10, 2015 for U.S. Appl. No. 14/160,798; 8 pages.
Notification to Grant dated May 25, 2015 for Chinese Application No. 201310084924.3; 5 pages.
Notice of Allowance dated Apr. 23, 2015 for European Application No. 12187209.7; 39 pages.
Communication Pursuant to Rules 70(2) and 70a(2) EPC and reference to Rule 39(1) EPC dated May 26, 2015 for European Application No. 14197698.5; 2 pages.
Image File Wrapper downloaded on May 21, 2015 for U.S. Appl. No. 14/041,484; 101 pages.
Office Action dated Aug. 6, 2014 for Chinese Application No. 201010624971.5; 17 pages.
Office Action dated Jun. 26, 2014 for Australian Application No. 2010235901, 4 pages.
Response to office action filed Jun. 1, 2015 for European Application No. 11869957.8; 10 pages.
Response to Office Action with English translation filed Feb. 2, 2015 for Chinese Application No. 201310064924.3; 23 pages.
Response to Office Action with English translation filed May 27, 2015 for Chinese Application No. 201180072455.9; 15 pages.
International Preliminary Report on Patentability dated Jan. 28, 2014 for PCT Application No. PCT/CN2011/077506; 8 pages.
Office Action dated May 4, 2015 for Canadian Application No. 2,646,037; 4 pages.
Notice of Allowance dated Jun. 25, 2015 for U.S. Appl. No. 14/324,380; 5 pages.
Response to Office Action filed Jul. 8, 2015 U.S. Appl. No. 14/160,798; 8 pages.
Office Action dated Jul. 23, 2015 for Chinese Application No. 201180072455.9; 7 pages.
Restriction Requirement dated Aug. 6, 2015 for U.S. Appl. No. 14/209,278; 5 pages.
Response to office action filed Aug. 7, 2015 for European Application No. 14197698.5; 27 pages.
Notice of Allowance dated Aug. 26, 2015 for U.S. Appl. No. 14/160,798; 12 pages.
Office Action dated May 29, 2015 for Canadian Application No. 2841601, 5 pages.
International Preliminary Report on Patentablity dated Sep. 24, 2015 for PCT Application No. PCT/US2014/027328; 12 pages.
Response to Office Action filed Sep. 30, 2015 for Chinese Application No. 201180072455.9; 6 pages.
International Preliminary Report of Patentability dated Oct. 26, 2015 for PCT Application No. PCT/US2014/019479, 8 pages.
Summons to Attend Oral Proceedings Pursuant to Rule 115(1) EPO dated Nov. 2, 2015 for European Application No. 08171185.5; 3 pages.
Response to Examiner's Report filed Nov. 4, 2015 for Canadian Application No. 2646037; 22 pages.
Decision to Grant dated Nov. 5, 2015 for Chinese Patent Application No. 201180072455.9; 6 pages.
Response to Examiner's Report filed Nov. 30, 2015 for Canadian Application No. 2,841,601; 11 pages.
Office Action dated Dec. 17, 2015 for U.S. Appl. No. 14/209,278; 6 pages.
Notice of Allowance dated Dec. 24, 2015 for U.S. Appl. No. 14/160,798; 6 pages.

\* cited by examiner

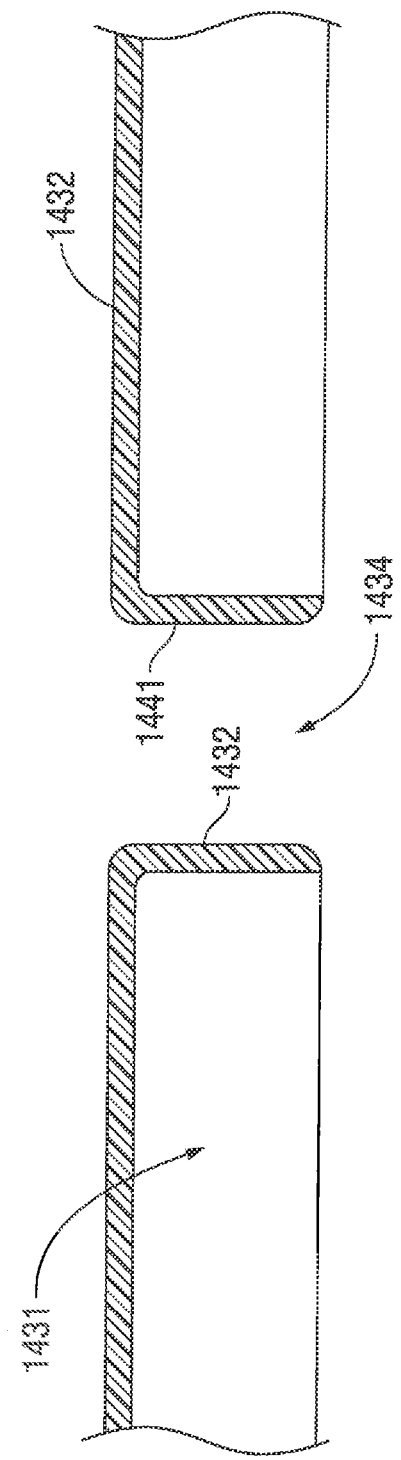

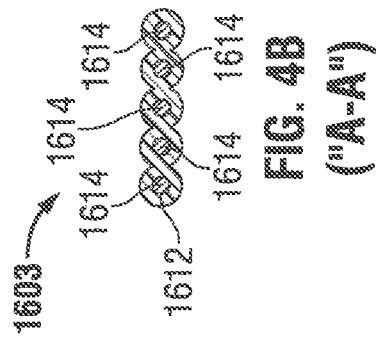
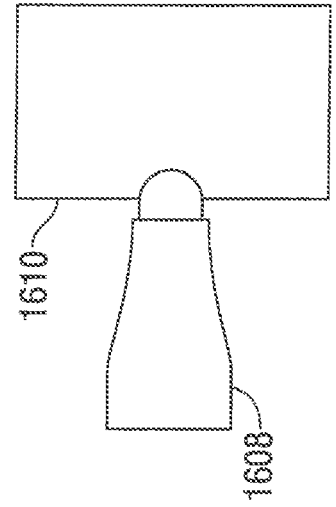
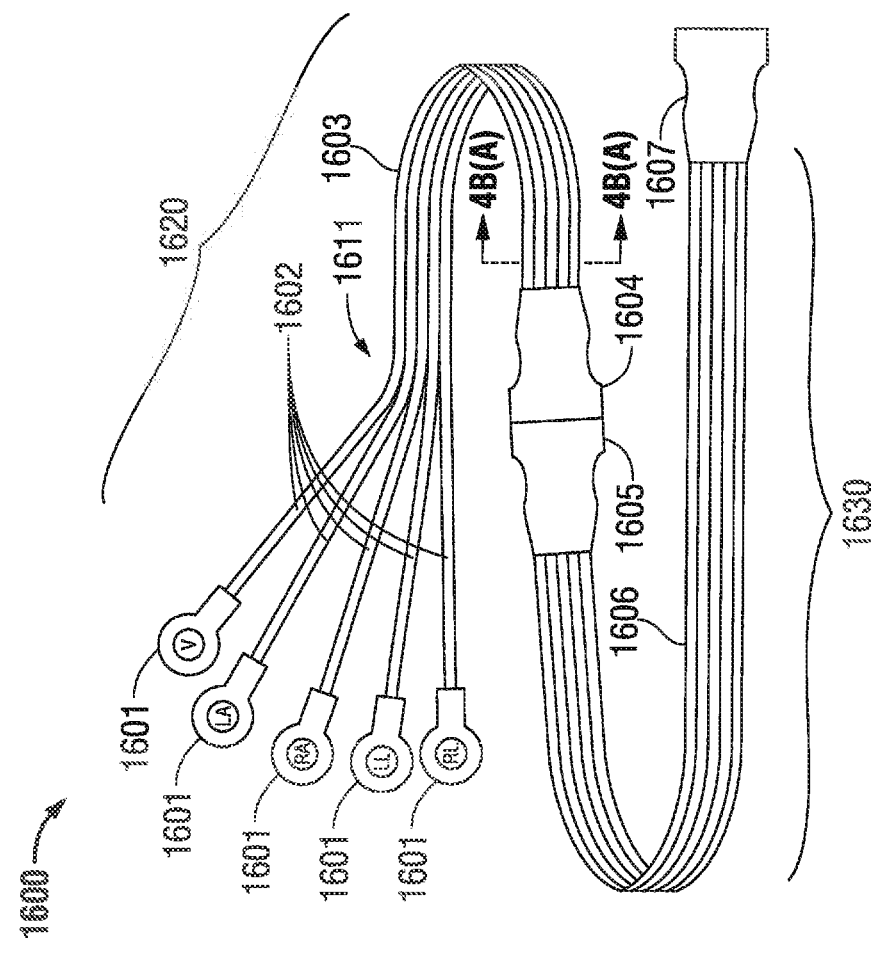
FIG. 4B ("A-A")
FIG. 4A

RADIOLUCENT ECG ELECTRODE SYSTEM

BACKGROUND

1. Technical Field

The present disclosure relates to biomedical electrodes, and in particular, to a radiolucent biomedical electrode connector and radiolucent lead wires for performing biomedical monitoring of a patent during imaging procedures.

2. Background of Related Art

Electrocardiograph (ECG) monitors are widely used to obtain medical (i.e., biopotential) signals containing information indicative of the electrical activity associated with the heart and pulmonary system. To obtain medical signals, ECG electrodes are applied to the skin of a patient in various locations. The electrodes, after being positioned on the patient, connect to an ECG monitor by a set of ECG lead wires. The distal end of the ECG lead wire, or portion closest to the patient, may include a connector which is adapted to operably connect to the electrode to receive medical signals from the body. The proximal end of the ECG lead set is operably coupled to the ECG monitor either directly or indirectly through an adapter, and supplies the medical signals received from the body to the ECG monitor.

A typical ECG electrode assembly may include an electrically conductive layer and a backing layer, the assembly having a patient contact side and a connector side. The contact side of the electrode pad may include biocompatible conductive gel or adhesive for affixing the electrode to a patient's body for facilitating an appropriate electrical connection between a patient's body and the electrode assembly. The connector side of the pad may incorporate a metallic press stud having a bulbous profile for coupling the electrode pad to the ECG lead wire. In use, the clinician removes a protective covering from the electrode side to expose the gel or adhesive, affixes the electrode pad to the patient's body, and attaches the appropriate ECG lead wire connector to the press stud by pressing or "snapping" the lead wire connector onto the bulbous press stud to achieve mechanical and electrical coupling of the electrode and lead wire. Alternatively, ECG connectors that engage via manipulation of a lever or other mechanical locking device may be employed. After use, a clinician then removes the ECG lead wire connector from the pad by pulling or "unsnapping" the connector from the pad or by releasing the lever or other locking mechanism.

Placement of the electrodes on a patient has been established by medical protocols. A common protocol requires the placement of the electrodes in a 5-lead configuration: one electrode adjacent each clavicle bone on the upper chest and a third electrode adjacent the patient's lower left abdomen, a fourth electrode adjacent the sternum, and a fifth electrode on the patient's lower right abdomen.

During certain procedures it may be necessary to monitor biological (e.g., ECG) parameters of a patient that is undergoing imaging, such as CT-scan or MRI. Use of conventional ECG connectors and lead wire sets typically associated therewith may have drawbacks in these applications, since they tend to interfere with the imaging systems. In one example, certain components of the ECG connectors and/or lead wires may be detected by the imaging apparatus and consequently may obfuscate the visual images upon which clinicians and surgeons rely. In another example, ferrous and/or magnetic components commonly found in ECG connectors, such as in springs and clips, may be potentially hazardous when used within the intense magnetic field of an MRI scanner.

SUMMARY

In an embodiment in accordance with the present disclosure, there is provided an ECG lead system that, in accordance with embodiments of the present disclosure, comprises a radiolucent ECG lead set assembly and an ECG lead extension assembly. The ECG lead set assembly comprises a radiolucent ECG lead set cable having at least one radiolucent conductor. At least one radiolucent electrode connector is operatively coupled to a distal end of the ECG lead set cable, and an ECG intermediate lead set connector is disposed at a proximal end of the ECG lead set cable. The ECG lead extension assembly comprises an ECG lead extension cable having at least one conductor. An ECG lead set extension connector is disposed at a distal end of the ECG lead extension cable, and a device connector is disposed at a proximal end of the ECG lead extension cable. The ECG intermediate lead set connector is configured to operatively couple to the ECG lead set extension connector. The device connector is configured to operatively couple to an ECG monitor.

A method of performing an ECG on a patient undergoing an imaging procedure is provided. In embodiments according to the present disclosure, the method comprises providing one or more radiolucent ECG connectors as described herein, providing a radiolucent ECG lead system as described herein, attaching one or more electrode pads to the body of a patient, operatively coupling the one or more radiolucent ECG connectors to a corresponding one of the one or more electrode pads, operatively coupling the device connector to an ECG monitor, and imaging the patient in an imaging apparatus selected from the group consisting of an MRI scanner, a CT scanner, and a PET scanner. The method in may include coupling the ECG intermediate lead set connector to the ECG lead set extension connector. Additionally or alternatively, the method may include providing an adapter configured to enable operable coupling of the device connector to an ECG monitor, coupling the device connector to the adapter, and coupling the adapter to the ECG monitor.

In another aspect, an ECG connector assembly in accordance with the present disclosure includes a housing having an opening defined therein configured to operably receive an electrode post of an ECG electrode pad. The ECG connector assembly includes an electrode member having a generally semicircular contact face and is disposed along at least a part of the perimeter of the opening. The ECG connector assembly includes an engagement member having an actuation surface and an engaging face. The engagement member is pivotable about a pivot to enable the engaging face to move from a first position whereby the engaging face is closer to the contact face and a second position whereby the engaging face is further from the contact face. A resilient radiused member joins a finger to a proximal end of the engagement member and is configured to bias the engagement member towards the first position. The ECG connector assembly includes a leadwire configured to operatively couple the electrode member to an ECG monitor.

In some embodiments, at least one of the electrode member or the leadwire is formed from radiolucent material. In some embodiments, the electrode member includes a junction block configured to facilitate operational coupling with the leadwire conductor. In some embodiments, the housing includes a retaining rib defining a cavity configured to retain the electrode member to the housing. In some embodiments, the actuating surface may include one or more ergonomic features, such as without limitation one or more scallops, one or more ridges, one or more grooves, knurling, contouring, a friction-enhancing surface, an elastomeric coating, an elastomeric grip, or a textured grip. In some embodiments, the ECG connector includes a bulkhead provided by the housing wherein the finger slidably engages the bulkhead when the engagement member moves between the first position and the second position. In some embodiments, the ECG connector assembly includes a channel configured to support a leadwire. The channel may includes an s-shaped strain relief portion configured to resist pullout of the leadwire. The ECG connector assembly may include a cover wherein at least a portion of the perimeter thereof includes a mating ridge, and a side wall extending from at least a portion of the perimeter of the housing and having a mating groove defined along a top surface thereof that is configured to engage the mating ridge of the cover. In some embodiments, the ECG connector assembly includes a female feature defined in the housing that is configured to receive a corresponding male projection, and a male projection extending from the cover that is configured to operably engage the female feature.

BRIEF DESCRIPTION OF THE DRAWINGS

Various embodiments of the present disclosure are described hereinbelow with references to the drawings, wherein:

FIG. 1C is a detail view of a press stud opening of the FIG. 1A embodiment of a radiolucent ECG electrode connector, in accordance with the present disclosure;

FIG. 4A is a view of an embodiment of a dual-section ECG electrode wiring harness, in accordance with the present disclosure;

FIG. 4B is a cross-sectional view of a portion of the dual-section ECG electrode wiring harness of FIG. 4A, as taken through A-A of FIG. 4A;

FIG. 5 is a view of a dual-section ECG electrode wiring harness in accordance with the present disclosure shown during use;

DETAILED DESCRIPTION OF EMBODIMENTS

Figure 1A:
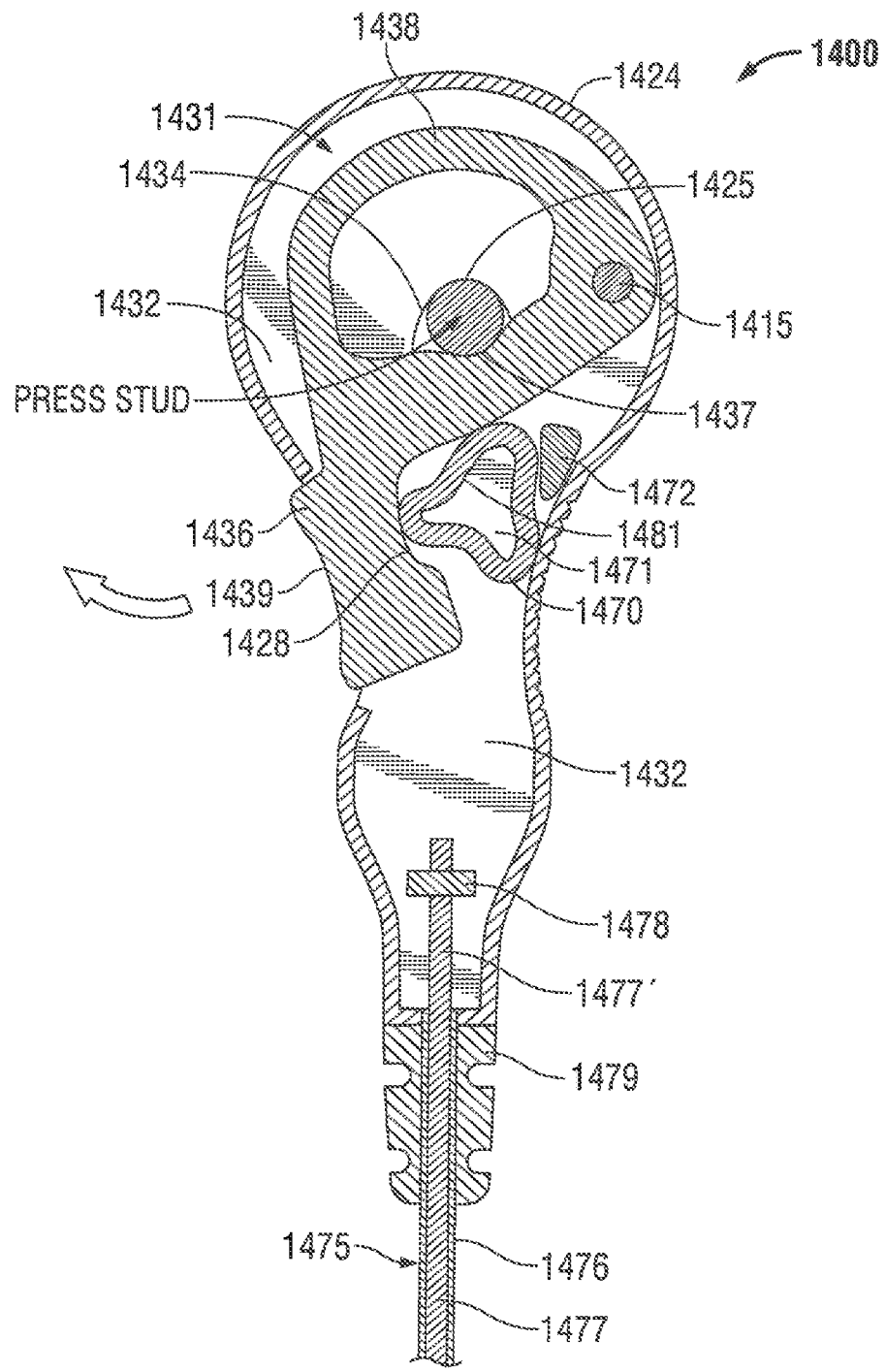
FIG. 1A is a view of an embodiment of a radiolucent ECG electrode connector in an engaged configuration, in accordance with the present disclosure.

Particular embodiments of the present disclosure are described hereinbelow with reference to the accompanying drawings; however, the disclosed embodiments are merely examples of the disclosure, which may be embodied in various forms. Well-known functions or constructions and repetitive matter are not described in detail to avoid obscuring the present disclosure in unnecessary or redundant detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In this description, as well as in the drawings, like-referenced numbers represent elements which may perform the same, similar, or equivalent functions.

In the drawings and in the descriptions that follow, the term "proximal," as is traditional, shall refer to the end of the instrument that is closer to a user, while the term "distal" shall refer to the end that is farther from a user. In addition, as used herein, terms referencing orientation, e.g., "top", "bottom", "up", "down", "left", "right", "clockwise", "counterclockwise", and the like, are used for illustrative purposes with reference to the figures and features shown therein. Embodiments in accordance with the present disclosure may be practiced in any orientation without limitation.

The present invention is directed to an electrode system suitable for use during patient imaging, such as during a CT-scan or MRI. Commonly available electrode connectors have components which may be detected on the image and/or may become dangerous when exposed to a particular field, such as a magnetic field.

Figure 1B:
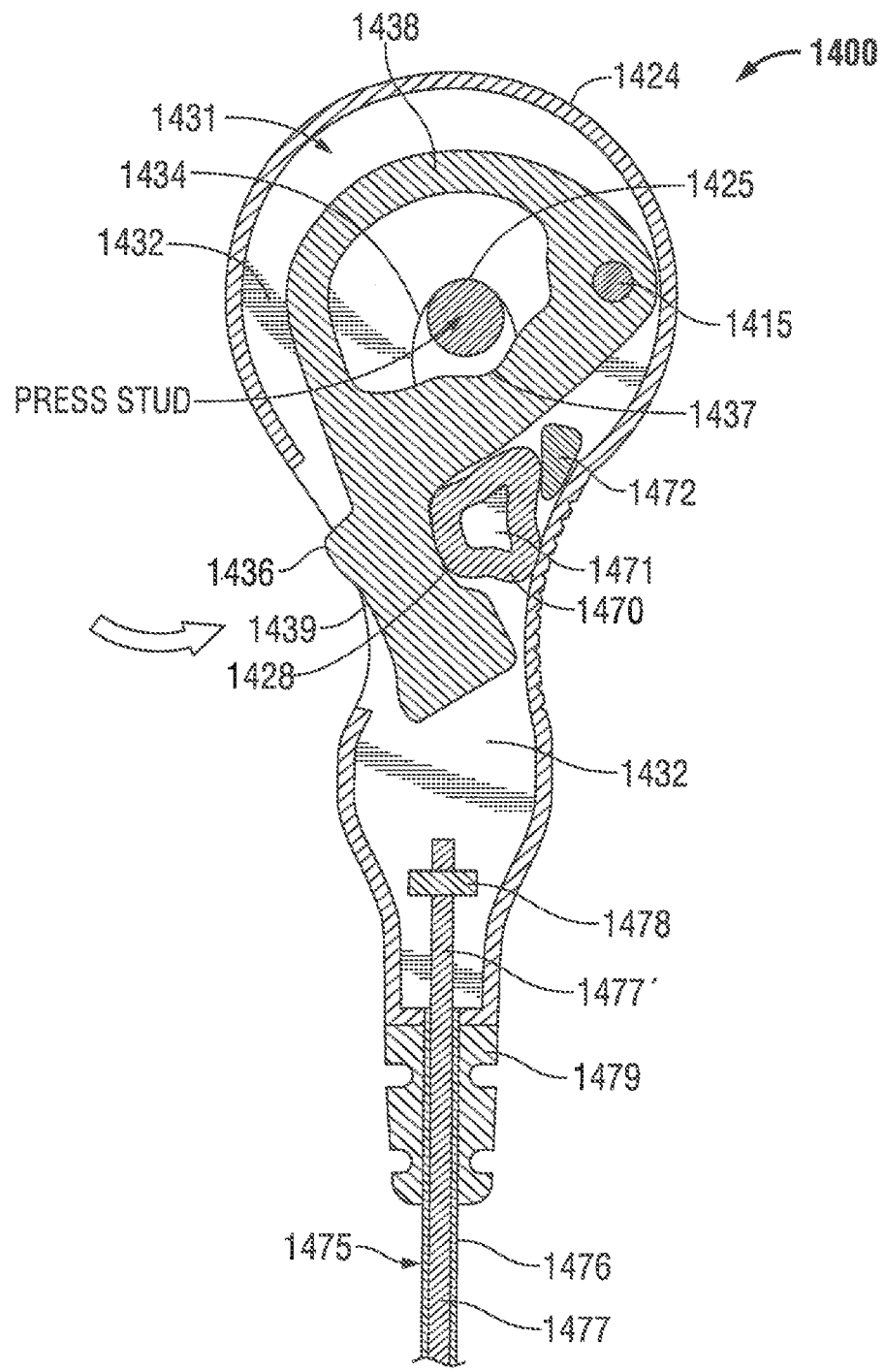
FIG. 1B is a view of the FIG. 1A embodiment in a disengaged configuration, in accordance with the present disclosure.

Accordingly, one aspect of the present invention provides an electrode connector which may be used during patient imaging. One embodiment of an ECG electrode connector of the present invention is shown in FIGS. 1A, 1B, and 1C. In view thereof, and so as not to obscure the present disclosure with redundant information, only those features distinct to ECG electrode connector 1400 will be described hereinafter.

ECG electrode connector 1400 is configured to facilitate the monitoring of ECG and other biological parameters while the subject patient is undergoing an imaging procedure, such as without limitation, MRI, CT, PET, and the like. Connector 1400 includes a housing 1424 having an interior recessed surface 1431 that includes an opening 1434 defined therein that opens to a patient-facing surface of the housing. Opening 1434 is dimensioned to accept the insertion of a head of a press stud of a patient electrode. Housing 1424 may be formed from any suitable non-conductive material, including polymeric materials. The connector 1400 includes an engagement member 1436 having an actuation surface 1439, which may be a contoured pushbutton, and an engaging face 1437. Engagement member 1436 is pivotable about a pivot 1415 to enable the engaging face 1437 to move from a first position whereby engaging face 1437 is disposed closer to a top portion 1425 of opening 1434 and a second position whereby engaging face 1437 is disposed further from a top portion 1425 of opening 1434. By this arrangement, the bulbous head of a press stud that has been introduced into opening 1434 may be captured in opening 1434 between engaging face 1437 and a sidewall of opening 1434. Engagement member 1436 includes a stiffener 1438, that may have an arcuate shape, disposed between engaging face 1437 and pivot 1415.

The interior recessed surface 1431 of housing 1424 includes a radiolucent conductor 1432 that facilitates the conduction of biological signals between a press stud captured within opening 1434 and a lead wire conductor 1477. Radiolucent conductor 1432 may be included within surface 1431 by any suitable manner, including without limitation, as a conductive coating and/or a conductive material incorporated within housing 1424 or associated portions thereof. In some embodiments, radiolucent conductor 1432 may be formed by dispersing conductive carbon powder over interior recessed surface 1431. The conductive carbon powder is then fused via the application of heat and/or pressure to the polymeric material that forms interior recessed surface 1431. In some embodiments, radiolucent conductor 1432 may be formed by the application of radiolucent conductive ink to interior recessed surface 1431. In other embodiments, the radiolucent conductor 1432 may comprise a carbon fiber wire fixed to the recessed surface 1431. As shown in FIG. 1C, radiolucent conductor 1432 may extend onto at least a portion of a sidewall 1441 of opening 1434.

ECG electrode connector 1400 includes a lead wire 1475 extending from a proximal (e.g., bottom) end thereof. Lead wire 1475 includes an outer insulator 1476 coaxially disposed about a conductor 1477. Conductor 1477 is formed from radiolucent electrically conductive material, such as conductive carbon or conductive carbon monofilament wire. In some embodiments, conductor 1477 is formed from one or more carbon fibers. A distal portion of the outer insulator is stripped thus exposing a distal portion of conductor 1477'. The exposed portion 1477' of conductor 1477 is operatively joined to radiolucent conductor 1432 of interior recessed surface 1431. Conductor 1477' may be joined by any suitable manner, including without limitation by a crimping element 1478 and/or by radiolucent electrically conductive adhesive. In some embodiments, the exposed portion 1477' of conductor 1477 and radiolucent conductor 1432 are integrally formed. A strain relief 1479 surrounds a portion of lead wire 1475 where lead wire 1475 exits the housing 1424.

A resilient member 1470 biases engagement member 1436 towards a first position whereby engaging face 1437 is closer to a top portion 1425 of opening 1434. Lobed resilient member 1470 is positioned between a recess 1428 defined in engagement member 1436 and a saddle 1472 provided by housing 1424. Resilient member 1470 may be formed from a radiolucent elastomer, including without limitation, silicone. Resilient member 1470 may have any shape to provide sufficient force to allow the desired movement of the engagement member 1436. The resilient member 1470 may have any regular or irregular shape, including circle, square, triangle, and clover.

In some embodiments, resilient member 1470 is a lobed member. In the embodiment shown in FIGS. 3A and 3B, lobed resilient member 1470 includes a three-lobe profile having each lobe evenly spaced at about 120° apart, however, a lobed resilient member 1470 in accordance with the present disclosure may include fewer than three lobes, or more than three lobes. Additionally or alternatively, lobed resilient member 1470 may include lobes that are not evenly spaced and/or irregularly placed. The resilient member may be solid throughout, or comprise one or more openings. Lobed resilient member 1470 includes a center opening 1471 defined therein and having a shape that generally corresponds to the contour of the perimeter (e.g., the lobe profile) of lobed resilient member 1470, and/or that may include one or more interior projections 1481. The ratio of the size of opening 1471 to the overall size of the lobed resilient member 1470 determines, at least in part, the resiliency of lobed resilient member 1470 and may facilitate tactile feedback to a user during the actuation/compression and release/extension of the combination of lobed resilient member 1470 and engagement member 1436. For example, and without limitation, cooperative interference between one or more interior projections 1481, as resilient member 1470 is compressed and/or released, may generate one or more vibrations that may, in turn, be sensed as tactile feedback by a user's fingertip via actuating surface 1439 and/or via housing 1424.

During use, a user may apply force to actuating surface 1439 using, e.g., a fingertip, thereby overcoming the biasing force of resilient member 1470 to cause engagement member 1436 to rotate slightly counterclockwise about pivot 1415. In turn, engaging face 1437 moves further from a top surface 1425 of opening 1434 which provides sufficient clearance to enable the introduction of a bulbous head of a press stud into opening 1434. Once the press stud is inserted into opening 1434, the user may remove finger pressure from actuating surface 1439, whereupon the biasing force of resilient member 1470 causes engagement member 1436 to rotate slightly clockwise about pivot 1415, thereby electromechanically engaging the press stud with a portion of opening 1434 and thus, electrically coupling the press stud with radiolucent conductor 1432 and conductor 1477.

Figure 2A:
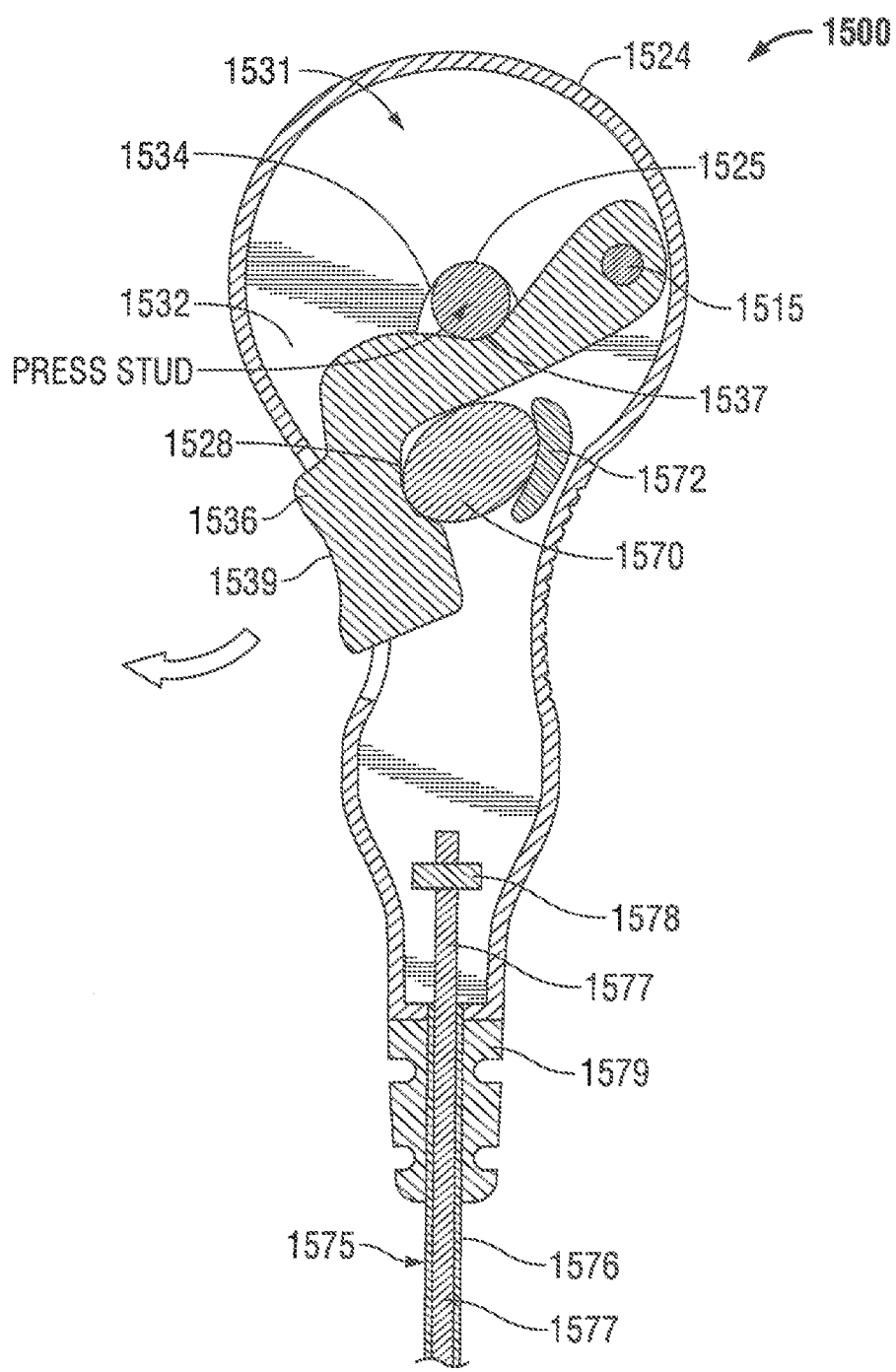
FIG. 2A is a view of another embodiment of a radiolucent ECG electrode connector in an engaged configuration, in accordance with the present disclosure.
Figure 2B:
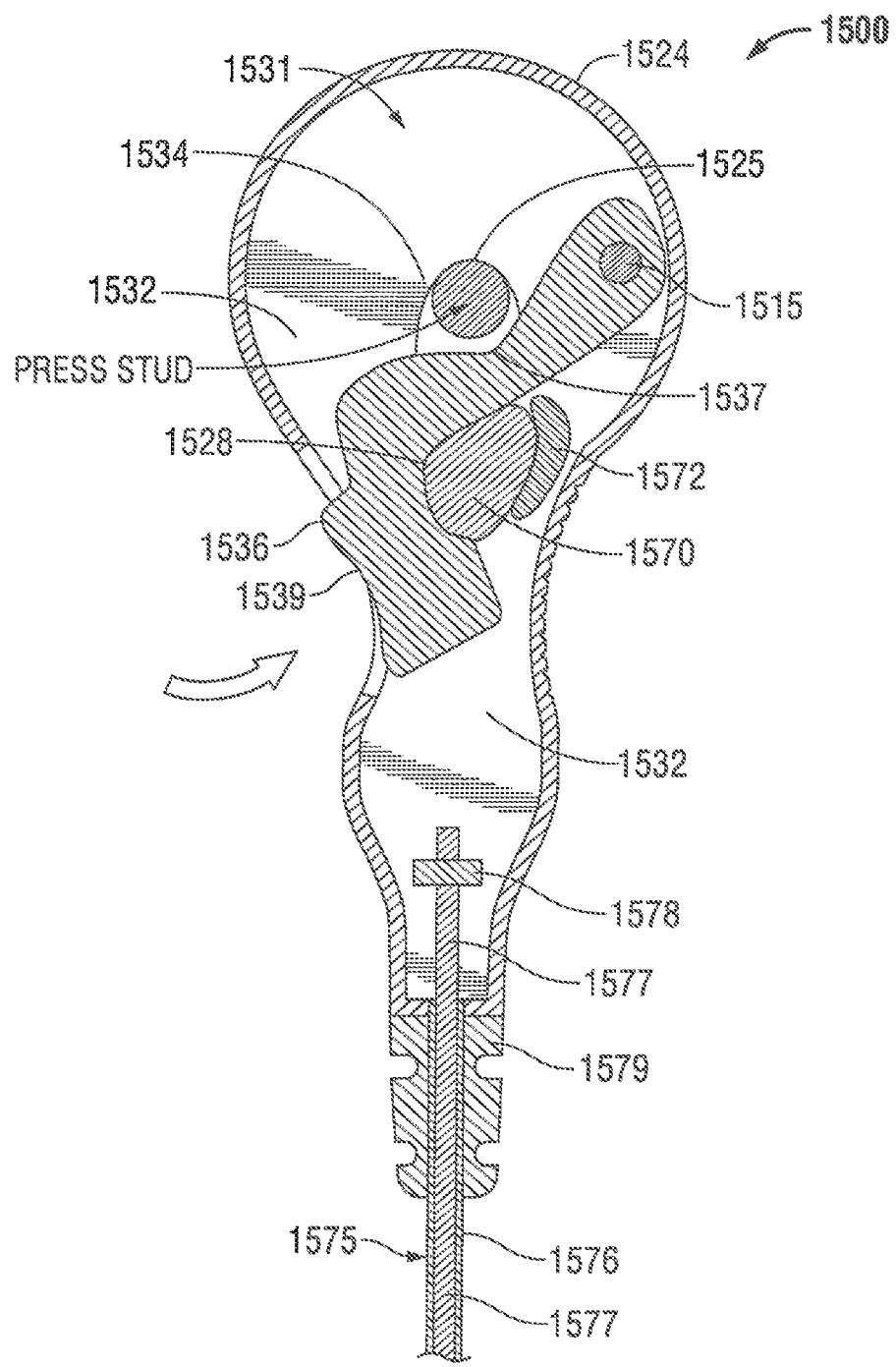
FIG. 2B is a view of the FIG. 2A embodiment in a disengaged configuration, in accordance with the present disclosure.

Yet another embodiment of a radiolucent ECG electrode connector is shown in FIGS. 2A and 2B and generally designated as 1500. In view thereof, and so as not to obscure the present disclosure with redundant information, only those features distinct to ECG electrode connector 1500 will be described hereinafter. Radiolucent electrode connector 1500 includes an engagement member 1536 having an actuation surface 1539, which may be a contoured pushbutton, and an engaging face 1537. Engagement member 1536 is pivotable about a pivot 1515 to enable the engaging face 1537 to move from a first position whereby engaging face 1537 is closer to a top portion 1525 of opening 1534 and a second position whereby engaging face 1537 is further from a top portion 1525 of opening 1534. By this arrangement, the bulbous head of a press stud that has been introduced into opening 1534 may be captured between engaging face 1537 and opening 1534. An interior recessed surface 1531 of housing 1524 includes a radiolucent conductor 1532 that facilitates the conduction of biological signals between a press stud captured within opening 1534 and a lead wire conductor 1577.

ECG electrode connector 1500 includes a lead wire 1575 extending from a proximal (e.g., bottom) end thereof. Lead wire 1575 includes an outer insulator 1576 coaxially disposed about a conductor 1477. Conductor 1477 is formed from radiolucent electrically conductive material, such as conductive carbon or conductive carbon monofilament wire. In some embodiments, conductor 1577 is formed from one or more carbon fibers. A distal portion of the outer insulator is stripped thus exposing a distal portion of conductor 1577'. The exposed portion 1577' of conductor 1577 is operatively joined to radiolucent conductor 1532 of interior recessed surface 1531. Conductor 1577' may be joined by any suitable manner, including without limitation by a crimping element 1578 and/or by radiolucent electrically conductive adhesive. In some embodiments, the exposed portion 1577' of conductor 1577 and radiolucent conductor 1532 are integrally formed. A strain relief 1579 surrounds a portion of lead wire 1575 where lead wire 1575 exits the housing 1524.

A resilient member 1570 biases engagement member 1536 towards a first position whereby engaging face 1537 is closer to a top portion 1525 of opening 1534. Resilient member 1570 may have any shape to provide sufficient force to allow the desired movement of the engagement member 1536. The resilient member 1570 may have any regular or irregular shape, including circle, square, triangle, ellipsoidal, and clover, and may, but need not be, solid throughout. In some embodiments resilient member 1570 has a generally spherical shape. Resilient member 1570 is positioned between a recess 1528 defined in engagement member 1536 and a saddle 1572 provided by a housing 1524. Resilient member 1570 may be formed from a radiolucent elastomer, including without limitation, silicone. In the embodiment shown in FIGS. 2A and 2B, resilient member 1570 may include surface or internal features, such as without limitation, ribs, voids, and/or textures that may facilitate tactile feedback to a user during the actuation/compression and release/extension of the combination of resilient member 1570 and engagement member 1536. In some embodiments resilient member 1570 may have a generally cylindrical shape, a generally ovoid shape, and/or or a compound shape that may include, e.g., a combination spherical, cylindrical, and/or ovoid shape. In some embodiments, resilient member 1570 may be hollow.

Figure 3:
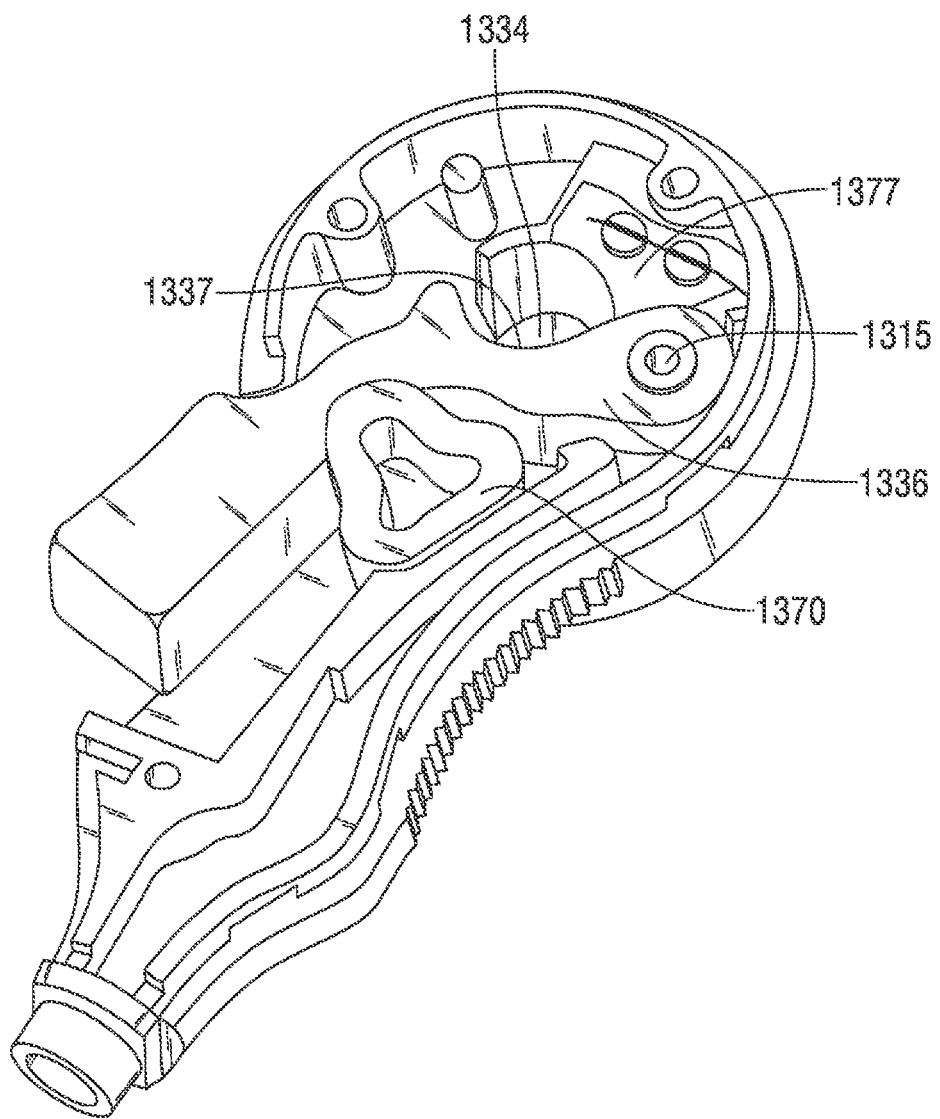
FIG. 3 is a view of another embodiment of a radiolucent ECG electrode connector, in accordance with the present disclosure
Figure 8:
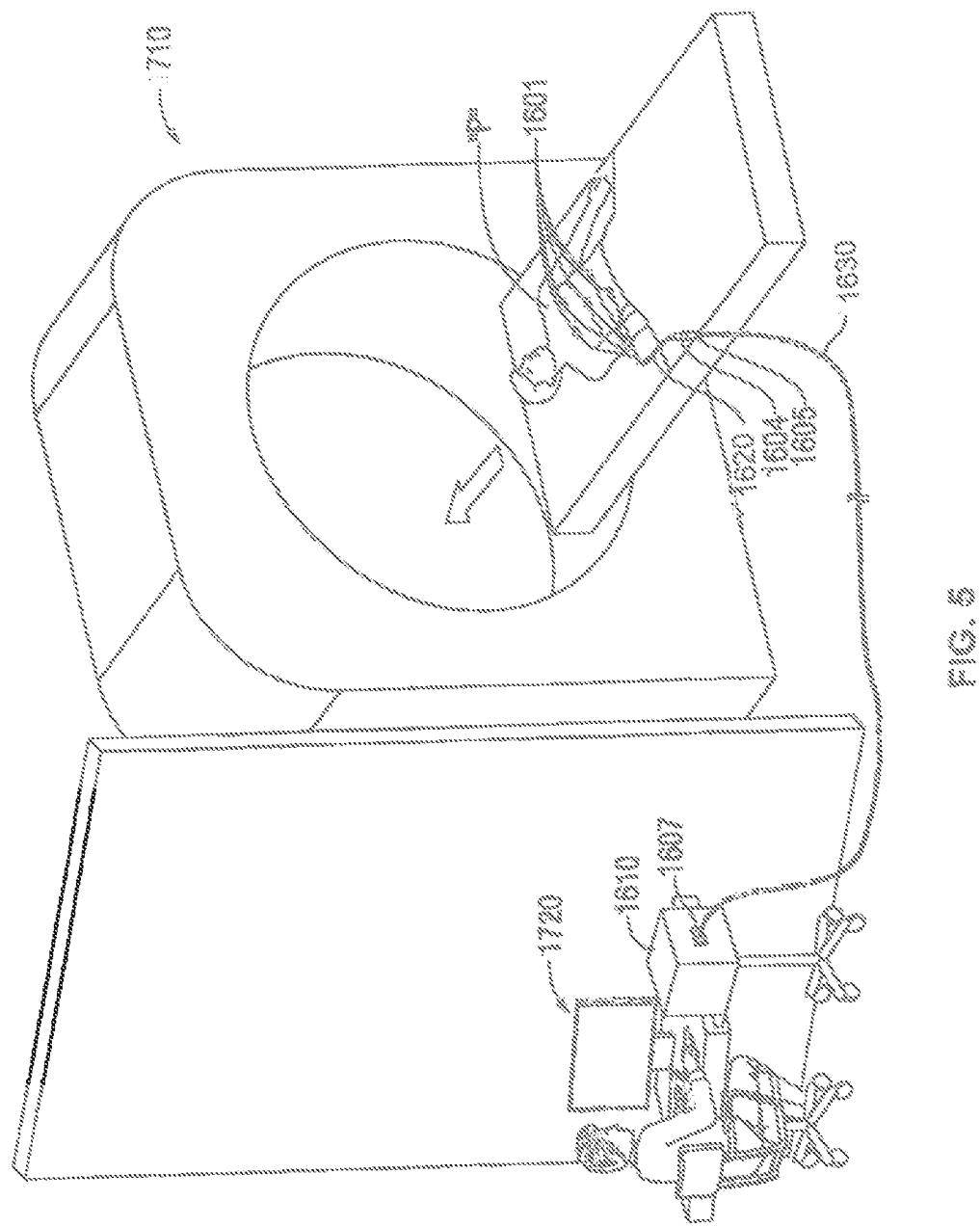

FIG. 3 shows in another embodiment of the present invention similar to the electrode connector shown in FIGS. 1A, 1B, and 1C and generally designated as 1300. In view thereof, and so as not to obscure the present disclosure with redundant information, only those features distinct to ECG electrode connector 1300 will be described hereinafter. As seen in FIG. 3, opening 1334 which is dimensioned to accept the insertion of a head of a press stud of a patient electrode is bounded on at least one side by a conductor 1377. Conductor 1377 may have any size and shape as long as at least a portion of the conductor extend into opening 1334 along at least a portion of sidewall 1334. In one embodiment, conductor 1377 extends through opening 1334 to completely cover at least a portion of the circumference of the opening 1334. Conductor 1377 may be made of a radiolucent conductive material such as a conductive polymer or a conductive carbon. A radiolucent leadwire (not shown) formed of a conductive carbon may be positioned in a passageway 1399 of the connector housing and joined to conductor 1377. In use, once an electrode stud is positioned in opening 1334 and engagement member 1336 is released, engagement face 1337 captures the electrode stud between the engagement face 1337 and a portion of conductor 1377.

Turning now to FIGS. 4A, 4B, and 5, another aspect of the present disclosure is illustrated wherein a radiolucent ECG lead system 1600 for use with an imaging system 1710 is provided. The radiolucent ECG lead system 1600 includes a radiolucent ECG lead set assembly 1620. Radiolucent ECG lead set assembly 1620 includes one or more radiolucent ECG lead set cables 1602 having a length, and one or more radiolucent electrode connectors 1601 operatively joined to a distal end of an ECG lead set cable 1603. The ECG lead set cables 1603 includes a plurality of individual radiolucent wires 1602, such as conductive carbon wires, arranged in a ribbon-cable configuration as shown in FIGS. 4A and 4B. The individual radiolucent wires 1602 separate from the ribbon 1603 at a separation point 1611 positioned between a distal end and a proximal end of radiolucent ECG lead set assembly 1620. It is understood that the separation point may vary and may be determined at the point of use, wherein the user separates the ribbon to a desired length for a particular application. In some embodiments, separation point 1611 is positioned about halfway between a distal end and a proximal end of radiolucent ECG lead set assembly 1620. In some embodiments, the one or more radiolucent electrode connectors include radiolucent ECG electrode connector 1400 and/or radiolucent ECG electrode connectors 1500, 1300. The one or more electrode connectors 1601 are configured to electrically connect to electrodes placed on a patient, and to an intermediate lead set connector 1604 disposed at a proximal end of the ECG lead set cable 1620.

The radiolucent ECG lead set cables 1602 include a center conductor 1614 and an outer insulator 1612. Center conductor 1614 is formed from a radiolucent electrically conductive material, including without limitation one or more carbon fibers. The one or more carbon fibers may be combined with other materials, including without limitation, polypropylene, polycarbonate, polyethylene, polyurethane, or polytetrafluoroethylene fibers to increase strength and/or flexibility of the conductor and the overall cable assembly 1620.

The ECG lead system 1600 further includes an ECG lead extension assembly 1630. ECG lead extension assembly 1630 includes an ECG lead extension cable 1606, which may be configured as a ribbon cable as shown in FIG. 4A, and/or may be configured in any other suitable cable arrangement. Lead extension cable 1606 may but need not be formed of radiolucent materials. In one embodiment, lead extension cable 1606 comprises wires formed of conventional tinned copper since it is outside of the imaging area. Limiting the use of radiolucent wires to areas within and adjacent the imaging area and connecting the radiolucent lead wires to a conventional lead extension cable may reduce the cost associated with providing longer radiolucent cables. Reducing the length of radiolucent lead wires may also increase durability since conventional tinned copper wires may be stronger than conductive carbon wires. In some embodiments, ECG lead extension cable 1606 may have a length greater that the length of the ECG lead set cable 1620.

An ECG lead set extension connector 1605 is disposed at a distal end of the ECG lead extension cable 1630. ECG lead set extension connector 1605 is configured and adapted to mate with and electrically connect to the intermediate lead set connector 1604 that is disposed at a proximal end of the ECG lead set cable 1620.

A device connector 1607 disposed at a proximal end of the ECG lead extension cable 1630. Device connector 1607 is configured and adapted to mate with and electrically connect to an ECG monitor 1610.

Additionally or alternatively, an adapter 1608 may be configured and adapted to mate with, and operably couple to, device connector 1607. Adapter 1608 is configured to enable operable coupling or interfacing between device connector 1607 and an ECG monitor 1610 that would otherwise be incompatible with the electrical or physical configuration of device connector 1607.

In use, as seen in FIG. 5, a patient "P" undergoing an imaging procedure by an imaging apparatus 1710 may be connected to an ECG monitor 1610 by ECG lead set assembly 1620. The ECG electrode connectors 1601 are coupled to press stud pads (not explicitly shown) attached to the patient "P". ECG lead set assembly 1620 is coupled via intermediate lead set connector 1604 and extension connector 1605 to ECG lead extension assembly 1630. ECG lead extension assembly 1630, in turn, is coupled to the ECG monitor 1610, which may be positioned in a control suite adjacent to imaging station 1720.

Figure 6:
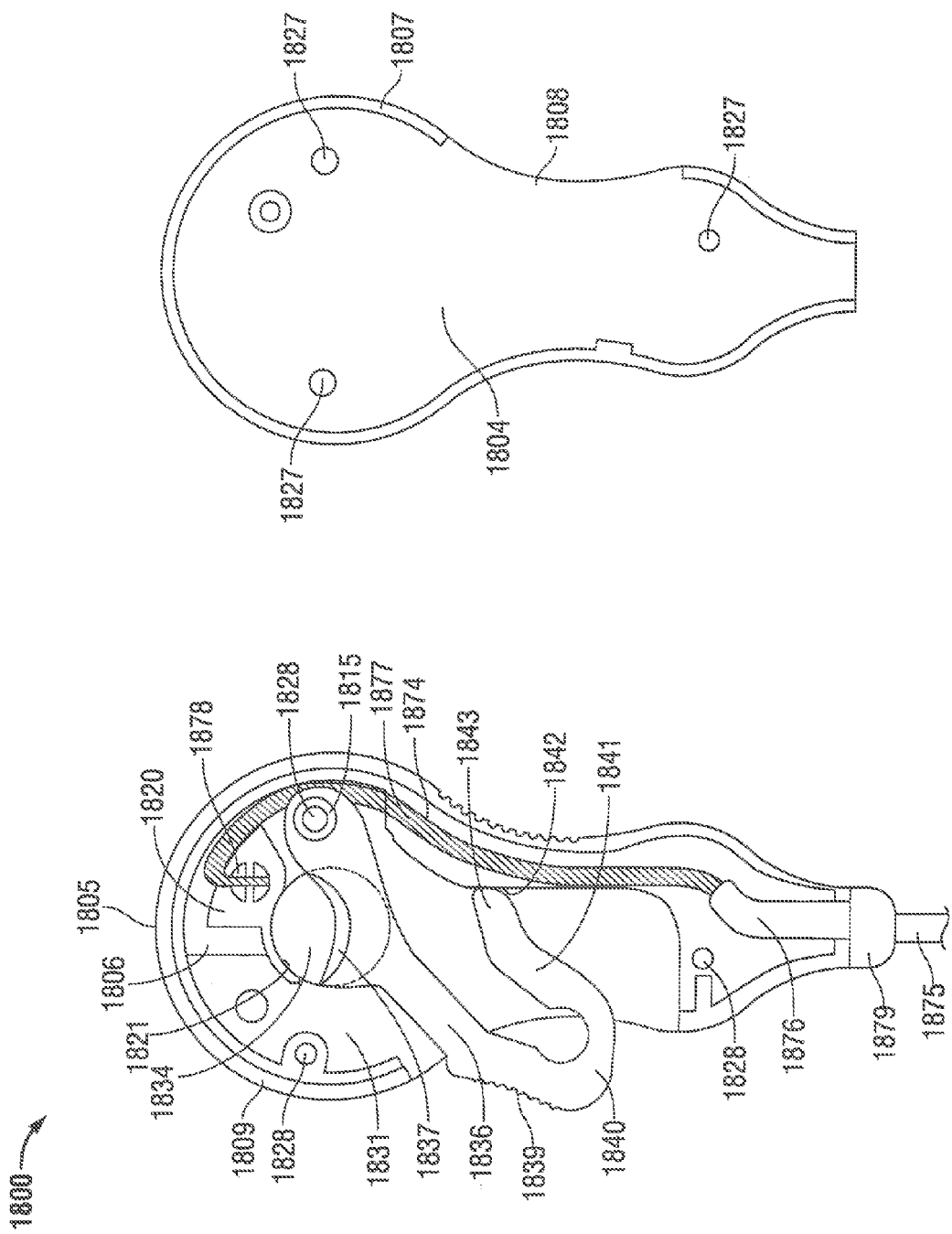
FIG. 6 is a view of another embodiment of an ECG electrode connector, in accordance with the present disclosure.
Figure 7A:
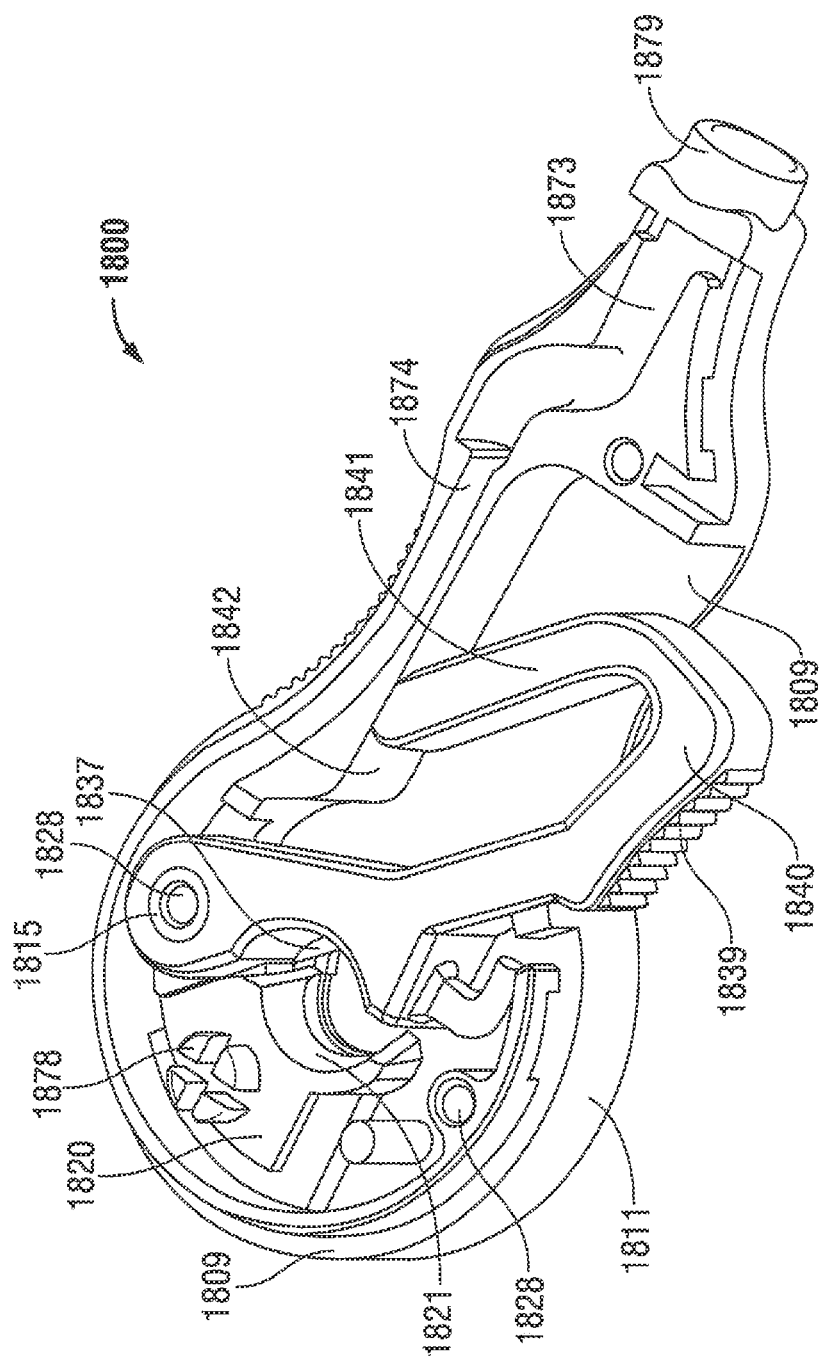
FIG. 7A is a top, perspective detail view of the FIG. 6 ECG electrode connector, in accordance with the present disclosure.
Figure 7B:
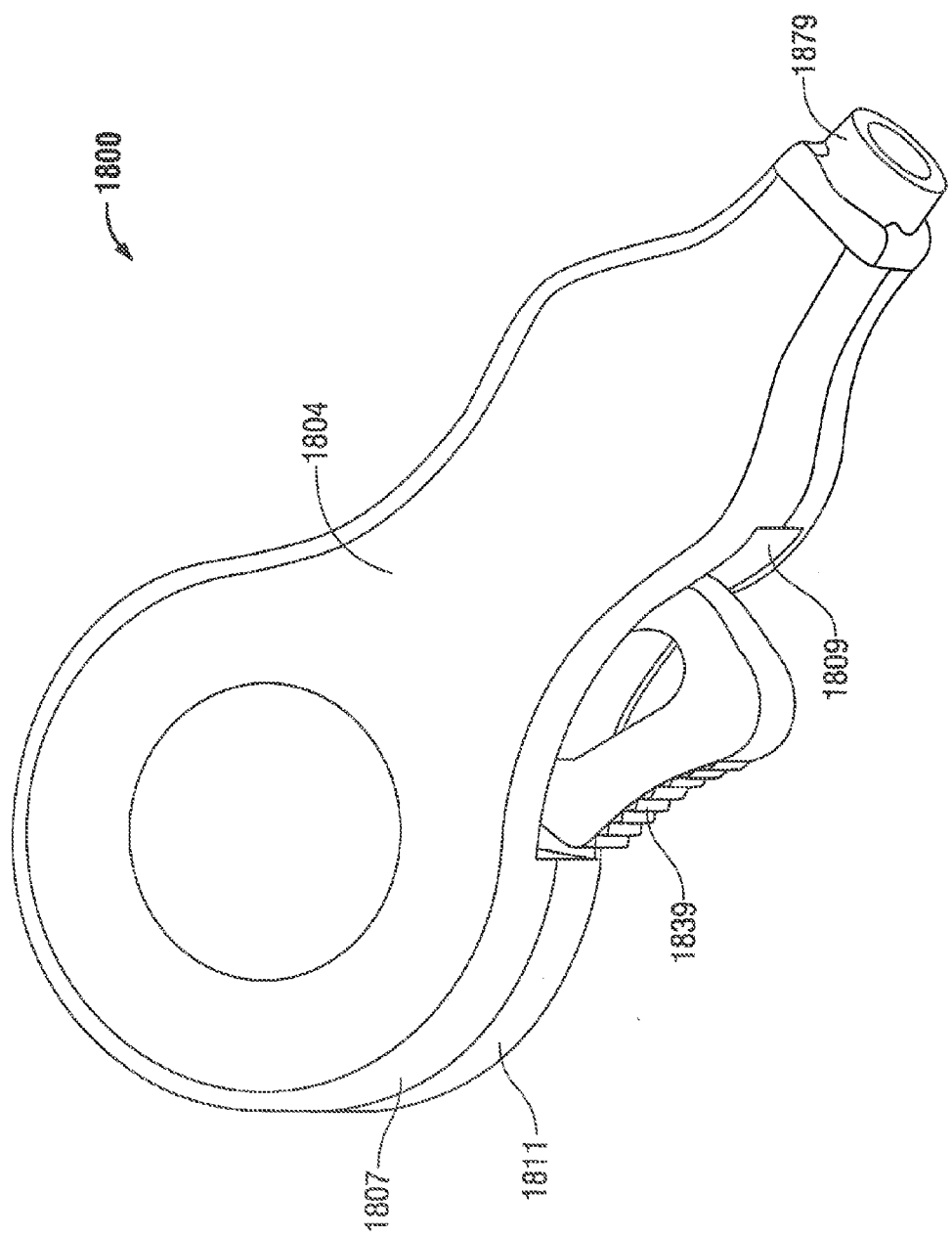
FIG. 7B is a bottom, perspective view of the FIG. 6 ECG electrode connector, in accordance with the present disclosure.

With reference now to FIGS. 6, 7A, and 7B, yet another embodiment of a radiolucent ECG electrode connector, in accordance with the present disclosure is described and generally designated as 1800. In view thereof, and so as not to obscure the present disclosure with redundant information, features distinct to the present embodiment are discussed. ECG electrode connector 1800 includes a housing 1805 having disposed therein an opening 1834 which is dimensioned to accept the insertion of a head of a press stud, electrode post, or similar electrode structure of a patient electrode, e.g., an ECG electrode pad. Housing 1805 is configured with one or more female features 1828 that are configured to receive one or more corresponding male features (e.g., "pins") provided by a cover 1804. At least a portion of the perimeter of housing 1805 includes a side wall 1811 extending therefrom that includes a mating groove 1809 along a top surface thereof that is configured to engage a corresponding mating ridge 1807 provided by at least a portion of the perimeter of cover 1804.

Housing 1805 includes an electrode member 1820 having a generally semicircular contact face 1821 that is disposed along at least a part of the perimeter of opening 1834. In some embodiments, contact face 1821 may have any size and shape, provided that at least a portion thereof extends into opening 1834 along at least a portion of the perimeter thereof. In some embodiments, contact face 1821 extends through opening 1834 to completely cover at least a portion of the circumference of the opening 1834. Electrode member 1820 and/or contact face 1821 may be formed from a radiolucent conductive material such as, without limitation, conductive polymer, conductive elastomeric material, conductive carbon, and/or carbon-impregnated substrate.

Electrode member 1820 includes a junction block 1878 that is configured to facilitate operational coupling (e.g., electrical, mechanical, electromechanical) with a leadwire conductor 1877. Advantageously, junction block 1878 may be formed from radiolucent material (e.g., conductive carbon). Electrode member 1820 and leadwire conductor 1877 may be joined using any suitable manner of connection, including without limitation, crimping, welding, brazing, overmolding, conductive adhesive.

In some embodiments, electrode member 1820 and leadwire conductor 1877 may be integrally formed. Housing 1805 includes at least one retaining rib 1806 that may provide additional support to electrode member 1820. In some embodiments, such as without limitation, those embodiments where electrode member 1820 is formed by overmolding, the at least one retaining rib 1806 defines a cavity into which overmolding material is deposited during the manufacturing process, which, in turn, reduces the complexity of molds and forms required to produce ECG electrode connector 1800.

A leadwire 1875 is received by housing 1805 via a strain relief 1879. Leadwire 1875 includes leadwire conductor 1877 coaxially disposed within a leadwire outer insulator 1876 (e.g., an insulating jacket). As best seen in FIG. 6, a distal portion of leadwire outer insulator 1876 is stripped away from leadwire 1875 to expose leadwire conductor 1877. The exposed portion of leadwire conductor 1877 is positioned in a channel 1874 defined in housing 1805 that provides support to leadwire conductor 1877 and positions the distal end thereof in alignment with junction block 1878 to facilitate a secure operable connection therewith. Channel 1874 includes an s-shaped feature 1873 that is configured to provide supplemental strain relief to leadwire 1875, e.g., to resist pullout. Advantageously, leadwire conductor 1877 and/or leadwire outer insulator 1876 are formed from radiolucent material, such as without limitation, conductive carbon.

ECG electrode connector 1800 includes an engagement member 1836 having an actuation surface 1839 and an engaging face 1837. As shown in FIGS. 6 and 7A, actuation surface 1839 may include one or more ergonomic features, including without limitation scallops, ridges, grooves, knurling, contouring, friction-enhancing surface(s), an elastomeric coating, an elastomeric grip, a textured grip, and/or the like. Engagement member 1836 is pivotable about a pivot 1815 to enable engaging face 1837 to move from a first position whereby engaging face 1837 is closer to contact face 1821 and a second position whereby engaging face 1837 is further from contact face 1821. By this arrangement, the head of a press stud and/or any portion of an electrode shaft that has been introduced into opening 1834 may be operably engaged between engaging face 1837 and contact face 1821 and thereby provide a robust electromechanical coupling between connector 1800 and an electrode of an ECG pad. At least a portion of the engagement member 1836, e.g., actuation surface 1839, extends to an exterior portion of housing 1805 through a cutout 1808 defined in cover 1804 and/or a cutout 1809 defined in a side wall 1811 of housing 1805.

A finger 1841 is joined to a proximal end of engagement member 1836 by a generally u-shaped resilient radiused member 1840. In some embodiments, engagement member 1836, resilient radiused member 1840, and/or finger 1841 are integrally formed. Engagement member 1836, resilient radiused member 1840, and finger 1841 are arranged to enable tip 1843 of finger 1841 to ride along bulkhead 1842 and thereby bias engagement member 1836 towards a first position whereby engaging face 1837 is closer to contact face 1821. Resilient radiused member 1840 may have any suitable shape, such as without limitation a u-shape as depicted in FIGS. 6 and 7A, a semicircular shape, a v-shape, and the like. Engagement member 1836, resilient radiused member 1840, and/or finger 1841 are configured to provide sufficient force to bias engagement member 1836 towards the first position to secure an electrode of an ECG pad (e.g., engaging face 1837 is closer to contact face 1821) yet enabling a user to readily depress actuation surface 1839 to effect the desired movement of the engagement member 1836 toward a second position to allow the an electrode of an ECG pad to be inserted into or released from the connector 1800.

It will be understood that various modifications may be made to the embodiments disclosed herein. Further variations of the above-disclosed and other features and functions, or alternatives thereof, may be desirably combined into many other different systems, instruments and applications. Various presently unforeseen or unanticipated alternatives, modifications, variations or improvements therein may be subsequently made by those skilled in the art, which are also intended to be encompassed by the following claims.

What is claimed is:

1. An ECG connector assembly, comprising:
a housing having an opening defined therein configured to operably receive an electrode post of an ECG electrode pad;
an electrode member having a generally semicircular contact face disposed along at least a part of the perimeter of the opening;
an engagement member having an actuation surface and an engaging face, and pivotable about a pivot to enable the engaging face to move from a first position whereby the engaging face is closer to the contact face and a second position whereby the engaging face is further from the contact face;
a resilient radiused member coupled between a finger and a proximal end of the engagement member to join the finger to the proximal end of the engagement member and configured to bias the engagement member towards the first position; and
a leadwire configured to operatively couple the electrode member to an ECG monitor.

2. The ECG connector assembly in accordance with claim 1, wherein at least one of the electrode member and the leadwire is formed from radiolucent material.

3. The ECG connector assembly in accordance with claim 1, the electrode member further having a junction block configured to facilitate operational coupling with a leadwire conductor.

4. The ECG connector assembly in accordance with claim 1, wherein the housing includes a retaining rib defining a cavity configured to retain the electrode member to the housing.

5. The ECG connector assembly in accordance with claim 1, wherein the actuation surface includes one or more ergonomic features.

6. The ECG connector assembly in accordance with claim 5, wherein the one or more ergonomic features are selected from the group consisting of one or more scallops, one or more ridges, one or more grooves, knurling, contouring, a friction-enhancing surface, an elastomeric coating, an elastomeric grip, or a textured grip.

7. The ECG connector assembly in accordance with claim 1, further comprising a bulkhead provided by the housing wherein the finger slidably engages the bulkhead when the engagement member moves between the first position and the second position.

8. The ECG connector assembly in accordance with claim 1, wherein the housing includes a channel configured to support a leadwire.

9. The ECG connector assembly in accordance with claim 8, the channel further including an s-shaped strain relief portion configured to resist pullout of the leadwire.

10. The ECG connector assembly in accordance with claim 1, further comprising:
a cover wherein at least a portion of a perimeter thereof includes a mating ridge; and
a side wall extending from at least a portion of a perimeter of the housing and having a mating groove defined along a top surface thereof that is configured to engage the mating ridge of the cover.

11. The ECG connector assembly in accordance with claim 10, further comprising:
a female feature defined in the housing that is configured to receive a corresponding male projection; and
a male projection extending from the cover that is configured to operably engage the female feature.

12. A radiolucent ECG connector assembly, comprising:
a radiolucent housing having an opening defined therein configured to receive an electrode post of an ECG electrode pad;
a radiolucent electrode member having a contact face disposed along at least a part of the perimeter of the opening;
a radiolucent engagement member having an actuation surface and an engaging face, and pivotable about a pivot to enable the engaging face to move from a first position whereby the engaging face is closer to the contact face and a second position whereby the engaging face is further from the contact face;
a radiolucent resilient member coupled between a radiolucent finger and a proximal end of the engagement member to join the radiolucent finger to the proximal end of the engagement member, wherein the resilient member is configured to bias the engagement member towards the first position; and
a radiolucent leadwire configured to operatively couple the electrode member to an ECG monitor.

13. The ECG connector assembly in accordance with claim 12, the electrode member further having a junction block configured to facilitate operational coupling with a leadwire conductor.

14. The ECG connector assembly in accordance with claim 12, wherein the housing includes a retaining rib defining a cavity configured to retain the electrode member to the housing.

15. The ECG connector assembly in accordance with claim 12, wherein the actuation surface includes one or more ergonomic features.

16. The ECG connector assembly in accordance with claim 15, wherein the one or more ergonomic features are selected from the group consisting of one or more scallops, one or more ridges, one or more grooves, knurling, contouring, a friction-enhancing surface, an elastomeric coating, an elastomeric grip, or a textured grip.

17. The ECU connector assembly in accordance with claim 12, further comprising a bulkhead provided by the housing wherein the finger slidably engages the bulkhead when the engagement member moves between the first position and the second position.

18. The ECG connector assembly in accordance with claim 12, wherein the housing includes a channel configured to support a leadwire.

19. The ECG connector assembly in accordance with claim 18, the channel further including an s-shaped strain relief portion configured to resist pullout of the leadwire.

20. The ECG connector assembly in accordance with claim 19, further comprising:
a cover wherein at least a portion of a perimeter thereof includes a mating ridge; and
a side wall extending from at least a portion of a perimeter of the housing and having a mating groove defined along a top surface thereof that is configured to engage the mating ridge of the cover.

* * * * *